United States Patent
Akiyama et al.

(10) Patent No.: US 10,994,271 B2
(45) Date of Patent: May 4, 2021

(54) MEMBRANE CARRIER FOR LIQUID SAMPLE TEST KIT, LIQUID SAMPLE TEST KIT, AND METHOD FOR PRODUCING LIQUID SAMPLE TEST KIT

(71) Applicant: Denka Company Limited, Tokyo (JP)

(72) Inventors: Yuto Akiyama, Machida (JP); Kenji Monden, Machida (JP)

(73) Assignee: Denka Company Limited, Tokyo (JP)

( * ) Notice: Subject to any disclaimer, the term of this patent is extended or adjusted under 35 U.S.C. 154(b) by 235 days.

(21) Appl. No.: 16/309,877

(22) PCT Filed: Jun. 13, 2017

(86) PCT No.: PCT/JP2017/021801
§ 371 (c)(1),
(2) Date: Dec. 13, 2018

(87) PCT Pub. No.: WO2017/217406
PCT Pub. Date: Dec. 21, 2017

(65) Prior Publication Data
US 2019/0329246 A1    Oct. 31, 2019

(30) Foreign Application Priority Data
Jun. 14, 2016    (JP) ............................. JP2016-118027

(51) Int. Cl.
*B01L 3/00* (2006.01)
*G01N 21/78* (2006.01)
*G01N 33/558* (2006.01)

(52) U.S. Cl.
CPC ..... *B01L 3/50273* (2013.01); *B01L 3/502746* (2013.01); *G01N 21/78* (2013.01);
(Continued)

(58) Field of Classification Search
CPC .......... B01L 3/50273; B01L 3/502746; B01L 2400/0406; B01L 2400/084; B01L 3/5023;
(Continued)

(56) References Cited

U.S. PATENT DOCUMENTS 5,458,852 A    10/1995    Buechler et al.
5,719,034 A    2/1998    Kiser et al.
(Continued)

FOREIGN PATENT DOCUMENTS

JP    S63-014783    4/1988
JP    H6-509424    10/1994
(Continued)

OTHER PUBLICATIONS

Rohrman BA, Leautaud V, Molyneux E, Richards-Kortum RR. A lateral flow assay for quantitative detection of amplified HIV-1 RNA. PLoS One. vol. 7 No. 9 e4561 (Year: 2012).*
(Continued)

*Primary Examiner* — Jennifer Wecker
*Assistant Examiner* — Jonathan Bortoli
(74) *Attorney, Agent, or Firm* — Leydig, Voit & Mayer, Ltd.

(57) ABSTRACT

The present invention provides a membrane carrier 3 for a test kit of detecting a target substance in a liquid sample, comprising at least one flow path 2 transporting the liquid sample, wherein a microstructure producing capillary action for transporting the liquid sample is formed at a bottom of the flow path 2, and the microstructure is provided to change along a transport direction d of the liquid sample.

14 Claims, 10 Drawing Sheets

(52) U.S. Cl.
CPC .... *G01N 33/558* (2013.01); *B01L 2400/0406* (2013.01); *B01L 2400/084* (2013.01)

(58) Field of Classification Search
CPC ...... G01N 21/78; G01N 33/558; G01N 37/00; G01N 33/543; G01N 33/54386; G01N 33/58
See application file for complete search history.

(56) References Cited

U.S. PATENT DOCUMENTS

| | | | |
|---|---|---|---|
| 7,824,611 B2* | 11/2010 | Buechler | G01N 33/558 435/287.1 |
| 2009/0111197 A1* | 4/2009 | Khan | B01L 3/502746 436/536 |
| 2010/0145294 A1 | 6/2010 | Song et al. | |
| 2010/0233708 A1 | 9/2010 | Mehra et al. | |
| 2010/0255512 A1 | 10/2010 | Wu et al. | |
| 2011/0143450 A1 | 6/2011 | White | |
| 2011/0284110 A1 | 11/2011 | Gagnon | |
| 2012/0042722 A1 | 2/2012 | Song et al. | |
| 2012/0225496 A1 | 9/2012 | Yoshida | |

FOREIGN PATENT DOCUMENTS

| | | | |
|---|---|---|---|
| JP | 2588174 | 3/1997 | |
| JP | H10-123137 | 5/1998 | |
| JP | 3513075 | 3/2004 | |
| JP | 2005-077301 | 3/2005 | |
| JP | 4597664 | 10/2005 | |
| JP | 2007-024498 | 2/2007 | |
| JP | 2009-241375 | 10/2009 | |
| JP | 2012-002806 | 1/2012 | |
| JP | 2012-505418 | 3/2012 | |
| JP | 5609648 | 4/2012 | |
| JP | 2012-524894 | 10/2012 | |
| JP | 5147011 | 2/2013 | |
| JP | 2013-053897 | 3/2013 | |
| JP | 2013053897 | * 3/2013 | ........... G01N 33/543 |
| JP | 2013-113633 | 6/2013 | |
| JP | 2013-148586 | 8/2013 | |
| JP | 2014-062820 | 4/2014 | |
| JP | 2014-081369 | 5/2014 | |
| JP | 2014-098715 | 5/2014 | |
| JP | 5799395 | 10/2015 | |
| JP | 2016-011943 | 1/2016 | |
| JP | 2017-040631 | 2/2017 | |
| WO | WO 93/024231 | 12/1993 | |
| WO | 2003/103835 | 12/2003 | |
| WO | 2009/096529 | 8/2009 | |
| WO | 2010/061598 | 6/2010 | |
| WO | 2010/122158 | 10/2010 | |
| WO | WO 2011/062157 | 5/2011 | |
| WO | 2016/051974 | 4/2016 | |
| WO | WO 2016/098740 | 6/2016 | |
| WO | WO 2018/181540 | 10/2018 | |
| WO | WO 2018/181549 | 10/2018 | |

OTHER PUBLICATIONS

U.S. Appl. No. 16/494,183, filed Sep. 13, 2019.
U.S. Appl. No. 16/494,232, filed Sep. 13, 2019.
International Preliminary Report on Patentability, dated Oct. 10, 2019, corresponding to International Application No. PCT/JP2018/012926 (filed Mar. 28, 2018), 8 pp.
International Preliminary Report on Patentability, dated Oct. 10, 2019, corresponding to International Application No. PCT/JP2018/012901 (filed Mar. 28, 2018), 9 pp.
Search Report and Written Opinion, dated Jun. 26, 2018, corresponding to International Application No. PCT/JP2018/012926 (filed Mar. 28, 2018), 8 pp.
Search Report and Written Opinion, dated Jun. 26, 2018, corresponding to International Application No. PCT/JP2018/012901 (filed Mar. 28, 2018), 9 pp.
Sirijarukul et al. (2007) "Flat sheet membrane with controlled variation of pore density and pore size in a direction parallel to the surface," Journal of Membrane Science 296(1-2):185-194.
International Preliminary Report on Patentability, dated Dec. 27, 2018, corresponding to International Application No. PCT/JP2017/021801 (filed Jun. 13, 2017), parent of the present application, 6 pp.
Search Report and Written Opinion, dated Jul. 18, 2017, corresponding to International Application No. PCT/JP2017/021801 (filed Jun. 13, 2017), parent of the present application, 2 pp.
Rivas, Lourdes (2014) "Improving Sensitivity of Gold Nanoparticle-Based Lateral Flow Assays by Using Wax-Printed Pillars as Delay Barriers of Microfluidics," Lab on a Chip, 14:4406-4414.
Extended European Search Report, dated Jan. 27, 2020, corresponding to European Application No. 17813302.1, 9 pp.

* cited by examiner (a)

(b)

(a)

(b)

(a)

(b)

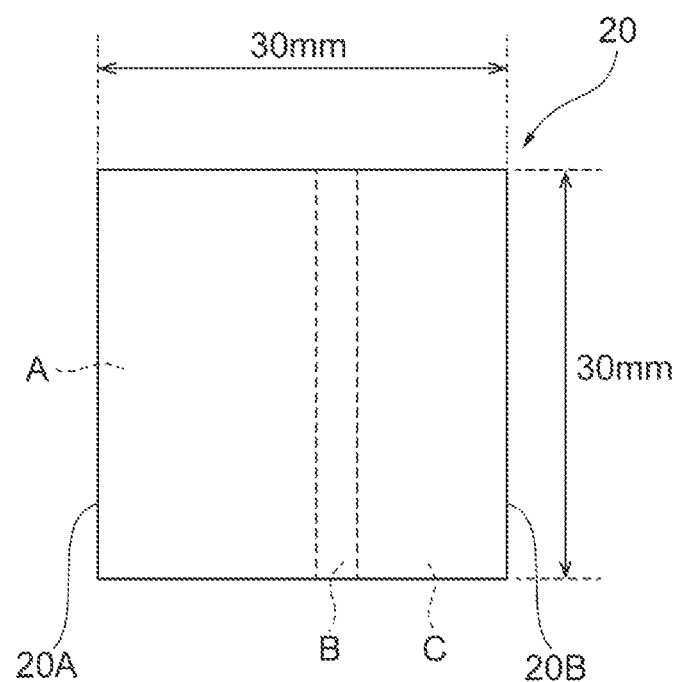

MEMBRANE CARRIER FOR LIQUID SAMPLE TEST KIT, LIQUID SAMPLE TEST KIT, AND METHOD FOR PRODUCING LIQUID SAMPLE TEST KIT

CROSS-REFERENCE TO RELATED APPLICATIONS

This application is a U.S. National Stage Application filed under 35 U.S.C. § 371 of International Application No. PCT/JP2017/021801, filed Jun. 13, 2017, which claims the benefit of Japanese Application No. JP 2016-118027, filed Jun. 14, 2016. Both of these applications are hereby incorporated by reference in their entireties.

TECHNICAL FIELD

The present invention relates to a membrane carrier for a liquid sample test kit involving a flow-rate change during a test, a liquid sample test kit using the carrier and a method for producing the test kit.

BACKGROUND ART

Recently, Point of Care Test (POCT) reagents using, for example, antigen-antibody reactions for determining contraction of infectious diseases, pregnancy, blood sugar level and the like have attracted attention. The POCT reagents have such characteristics as capability of determination of test results in a short time, simple operation and low cost. By virtue of these characteristics, the POCT reagents are frequently used in, for example, medical examinations at the stage of mild symptoms and regular medical examinations and used as an important examination tool in home medical care which is expected to expand from now on.

In most POCT reagents, determination is made by introducing a liquid sample such as blood in a test kit and detecting a predetermined target substance contained in the liquid sample. As a method for detecting a predetermined target substance from a liquid sample, immunochromatography is frequently used. The immunochromatography is a technique for detecting a substance by delivering a liquid drop onto a membrane carrier of a test kit, allowing the liquid drop to move on the membrane carrier, allowing a target substance to bind to a label and the resultant to further bind specifically to a substance (hereinafter referred to as a detection substance) immobilized in the test kit to produce a color or weight change, and detecting the change. The detection substance may be called also as a reagent.

As a technique for detecting a target substance, a technique for detecting a color change produced by using colored latex particles, fluorescent latex particles, metallic colloidal particles and the like as a label by an optical measuring apparatus such as an absorbance measuring apparatus is well known.

As the POCT reagent for optically determining a color change, lateral flow type kit using a nitrocellulose membrane is often used (Patent Literature 1). The nitrocellulose membrane has many micropores having a diameter of about several Lm and a liquid sample moves through the micropores with the help of capillary force.

However, the nitrocellulose membrane, which is derived from a natural product, has pores not uniform in size and arrangement. Because of this, the flow rate of a liquid sample varies depending on the membranes. If the flow rate varies, the time taken for detecting a target substance varies, with the result that a wrong determination: "binding was not detected" may be made before the target substance binds.

In order to overcome the above problem, a technique for artificially producing a micro flow-path is devised (Patent Literatures 2 to 6). If this technique is used, a membrane carrier having a uniform structure can be prepared, with the result that the possibility of wrong determination: "binding was not detected" made before the target substance binds, can be reduced.

CITATION LIST

Patent Literature

Patent Literature 1: Japanese Unexamined Patent Publication No. 2014-062820
Patent Literature 2: Japanese Patent No. 4597664
Patent Literature 3: Japanese Unexamined Patent Publication No. 2012-524894
Patent Literature 4: Japanese Patent No. 5609648
Patent Literature 5: Japanese Unexamined Patent Publication No. 2016-011943
Patent Literature 6: Japanese Unexamined Patent Publication No. 2013-113633
Patent Literature 7: U.S. Patent Application Publication No. 2011/0284110

SUMMARY OF INVENTION

Technical Problem

However, the techniques described in the above Patent Literatures, by which uniform flow-path structures are formed in the systems, fail to form the structures satisfying functions varying in individual portions in the flow path (for example, a portion for sufficiently mixing a liquid and a portion for immediately developing a liquid); in short, form "one structure-fits-all". As a result, the performance of the system was not sufficiently provided. To describe more specifically, as the flow rate of a liquid sample decreases, the sensitivity of a test kit (how low level of a target substance can be detected) increases; however, in this case, determination time (time until stabilization of a change produced by a target substance detected) becomes long. A structure satisfying these two characteristics has not been produced.

In particular, the lateral-flow immunochromatography has a simple detection system. Because of the simplicity, a flow-path structure tends to influence test results. Patent Literature 7 reports that the flow rate of a liquid sample changes depending on the flow-path structure; however, the literature is silent about the effect produced by the flow-rate change.

The present invention was made in view of the aforementioned problems and is directed to provide a test kit enabling highly sensitive detection in a short time by immunochromatography which can optically determine that a target substance is detected.

Solution to Problem

More specifically, the present invention is as follows:
(1) A membrane carrier for a liquid sample test kit of detecting a target substance in a liquid sample, comprising at least one flow path transporting the liquid sample, in which a microstructure producing capillary action for transporting the liquid sample is formed at the bottom of the flow path, and the microstructure is provided to change along the transport direction of the liquid sample.

(2) The membrane carrier for a liquid sample test kit according to (1), in which the microstructure is provided such that the flow rate of the liquid sample in the flow path changes within the flow path.

(3) The membrane carrier for a liquid sample test kit according to (1) or (2), in which the microstructure is provided such that a ratio of the highest flow rate to the lowest flow rate of the liquid sample in the flow path is 1 or more and 10 or less.

(4) The membrane carrier for a liquid sample test kit according to any one of (1) to (3), in which the microstructure is provided such that both of a lowest flow rate and a highest flow rate of the liquid sample in the flow path are 0.30 mm/s or more and 5.0 mm/s or less.

(5) The membrane carrier for a liquid sample test kit according to any one of (1) to (4), in which a height of the microstructure in the flow path is 10 μm or more and 500 μm or less.

(6) The membrane carrier for a liquid sample test kit according to any one of (1) to (5), in which a bottom area of the microstructure in the flow path is 75 μm$^2$ or more and 250000 μm$^2$ or less.

(7) The membrane carrier for a liquid sample test kit according to any one of (1) to (6), in which a nearest distance between the microstructures in the flow path is 500 μm or less.

(8) The membrane carrier for a liquid sample test kit according to any one of (1) to (7), in which an aspect ratio of the microstructure is 0.1 or more and 2.0 or less.

(9) A liquid sample test kit for detecting a target substance in a liquid sample, comprising the membrane carrier for a liquid sample test kit according to any one of (1) to (8), in which the membrane carrier comprises a detection zone for detecting a target substance in a liquid sample, and when the target substance is detected in the detection zone, a color change with which the detection can be confirmed by optical means occurs.

(10) The liquid sample test kit according to (9), in which a label comprising an antibody or an antigen-binding fragment thereof specifically reacting with the target substance in the liquid sample is provided in at least a part of the liquid sample test kit to be able to react with the target substance, and the color change is produced by the label bound to the target substance.

(11) The liquid sample test kit according to (10), in which the label is a particle comprising a colored latex particle or a fluorescent latex particle to which the antibody or the antigen-binding fragment thereof binds.

(12) The liquid sample test kit according to (10) or (11), in which a detection substance detecting the target substance is immobilized in the detection zone, and the color change is produced by holding the label by the detection substance in the detection zone to produce a color.

(13) A method for producing a liquid sample test kit according to any one of (9) to (12), comprising immobilizing, to the detection zone, a detection substance producing the color change by holding the target substance in the detection zone.

(14) A method for testing a liquid sample using the liquid sample test kit according to any one of (9) to (12), comprising:

preparing a mixed liquid sample by mixing the liquid sample and a label specifically binding to a target substance in the liquid sample to mutually bind the target substance and the label;

delivering a drop of the mixed liquid sample to a drop zone provided in the membrane carrier;

transporting the mixed liquid sample from the drop zone to the detection zone by the microstructure; and detecting a color change in the detection zone.

Advantageous Effects of Invention

According to the present invention, it is possible to provide a test kit enabling highly sensitive detection in a short time by immunochromatography which can optically determine that a target substance is detected.

BRIEF DESCRIPTION OF DRAWINGS

FIG. 10 shows a schematic view of a mold for forming a microstructure which is an embodiment of the present invention.

DESCRIPTION OF EMBODIMENTS

Embodiments of the present invention will be described below.

The membrane carrier for a liquid sample test kit according to an embodiment refers to, for example, a membrane carrier for a liquid sample test kit, which detects a target substance in the liquid sample.

The target substance herein, which is not limited, may be any substance as long as it can undergo an antigen-antibody reaction with various pathogens, various clinical markers and antibodies. Examples of the target substance include, but are not particularly limited to, antigens of viruses such as influenza virus, norovirus, adenovirus, RS virus, HAV, HBs and HIV; antigens of bacteria such as MRSA, Group-A *streptococcus*, Group-B *streptococcus* and *Legionella* bacteria; toxins produced by bacteria, *Mycoplasma, Chlamydia trachomatis*, hormones such as human chorionic gonadotropin; and C reactive protein, myoglobin, myocardial troponin, various tumor markers, agrochemicals and environmental hormones. If the target substance is particularly a substance that must be quickly detected and treated, such as influenza virus, norovirus, C reactive protein, myoglobin and myocardial troponin, the liquid sample test kit and membrane carrier according to the embodiment are extremely useful. The target substance may be an antigen, which solely induces an immune response, or may be a hapten, which cannot induce an immune response by itself but can induce an immune response if it binds to an antibody through an antigen-antibody reaction. The target substance is usually suspended or dissolved in a liquid sample. The liquid sample may be a sample obtained by suspending or dissolving the target substance in, for example, a buffer solution.

Figure 1:
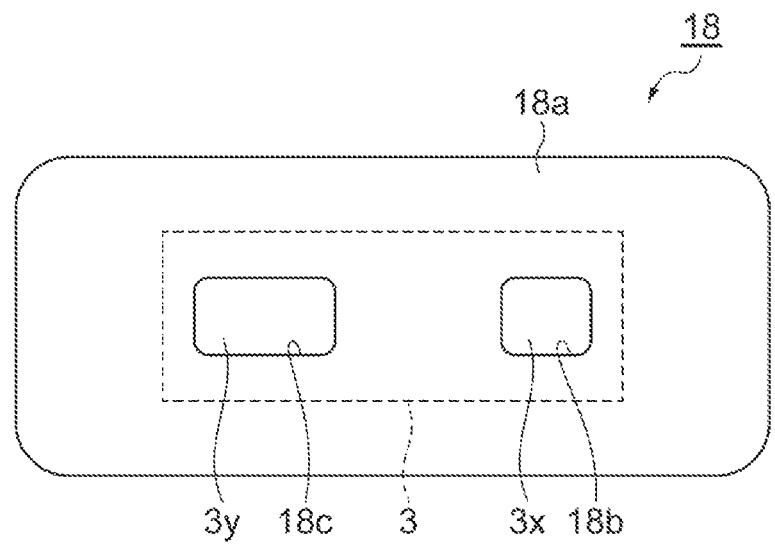
FIG. 1 shows a schematic top view of a test kit which is an embodiment of the present invention.

The liquid sample test kit according to the embodiment (hereinafter referred to also simply as the "test kit") detects a target substance in a liquid sample. FIG. 1 is a schematic top view of a test kit. For example, as shown in FIG. 1, a test kit 18 has a membrane carrier 3 and a case 18a for accommodating the membrane carrier 3. The membrane carrier 3 has, in the surface thereof, a drop zone 3x on which a drop of a liquid sample is delivered and a detection zone 3y for detecting a target substance in a liquid sample. The drop zone 3x is exposed in a first opening 18b of the case 18a. The detection zone 3y is exposed in the second opening 18c of the case 18a.

Figure 2:
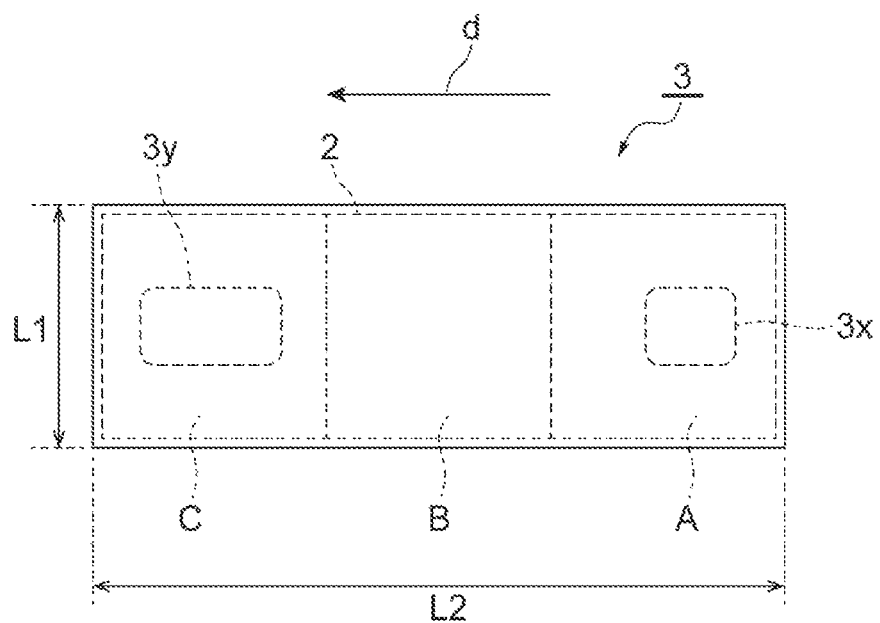
FIG. 2 shows a schematic top view of a membrane carrier which is an embodiment of the present invention.

FIG. 2 is a schematic top view of the membrane carrier 3. As shown in FIG. 2, the membrane carrier 3 has at least one flow path 2 for transporting a liquid sample. At the bottom of the flow path 2, a microstructure is provided (not shown, details will be described later). The microstructure is present at least between the drop zone 3x and the detection zone 3y. The microstructure may be provided over the entire surface of the membrane carrier 3. The entire surface of the membrane carrier 3 may serve as the flow path 2 for a liquid sample. Owing to the microstructure, capillary action is produced. A liquid sample is transported from the drop zone 3x to the detection zone 3y (along transport direction d) through the microstructure with the help of the capillary action produced by the microstructure. When a target substance in a liquid sample is detected in the detection zone 3y, the color of the detection zone 3y changes.

The entire shape of the membrane carrier 3 is not particularly limited; however, the shape may be, for example, a polygon such as a rectangle, a circle or an ellipsoid. If the membrane carrier 3 is a rectangle, the length (length of the shorter side) L1 of the membrane carrier 3 may be, for example, 2 mm or more and 100 mm or less and the width (length of the longer side) L2 of the membrane carrier 3 may be, for example, 2 mm or more and 100 mm or less. The thickness of the membrane carrier excluding the heights of the microstructure, may be, for example, 0.1 mm or more and 10 mm or less.

The microstructure is provided to change along, for example, the transport direction d of a liquid sample. In other words, the membrane carrier 3 has a plurality of regions (a first region A, a second region B and a third region C arranged in this order from the drop zone) and adjacent regions (first region A and second region B; and second region B and third region C) have mutually different microstructures.

FIGS. 3 to 6 each show a microstructure provided at the bottom of the flow path according to the embodiment and an example of convex portions constituting the microstructure. In each of FIGS. 3 to 6, (a) is a plan view (top view) of microstructure; and (b) is a perspective view of one of the convex portions constituting the microstructure. As shown in FIGS. 3 to 6, a microstructure 7 is an assembly of convex portions 8. More specifically, the membrane carrier 3 has a flat part 9 corresponding to the bottom of the flow path 2 of a liquid sample and a plurality of convex portions 8 corresponding to the flat part 9. The space between the convex portions 8 serves as flow path 2 for transporting a liquid sample along the surface of the membrane carrier 3 with the help of capillary action. In other words, space in the microstructure 7 serves as the flow path 2 for transporting a liquid sample along the surface of the membrane carrier 3 by capillary action. The convex portions 8 may be arranged on the surface of the membrane carrier 3 in a regular manner or a translational symmetric manner.

Figure 3:
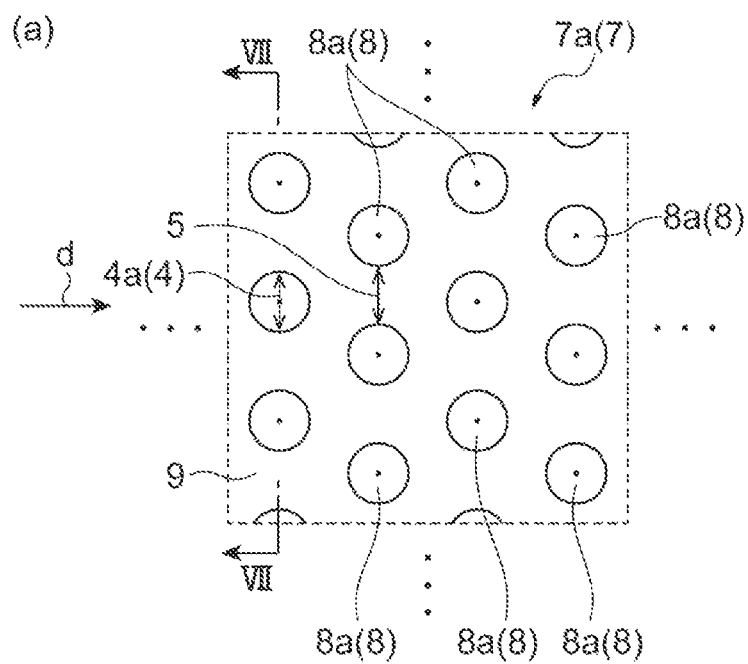
FIG. 3 shows (a) a plan view (top view) of microstructures which is an embodiment of the present invention; and (b) a perspective view of a convex portion constituting the microstructure shown in (a).
Figure 3:
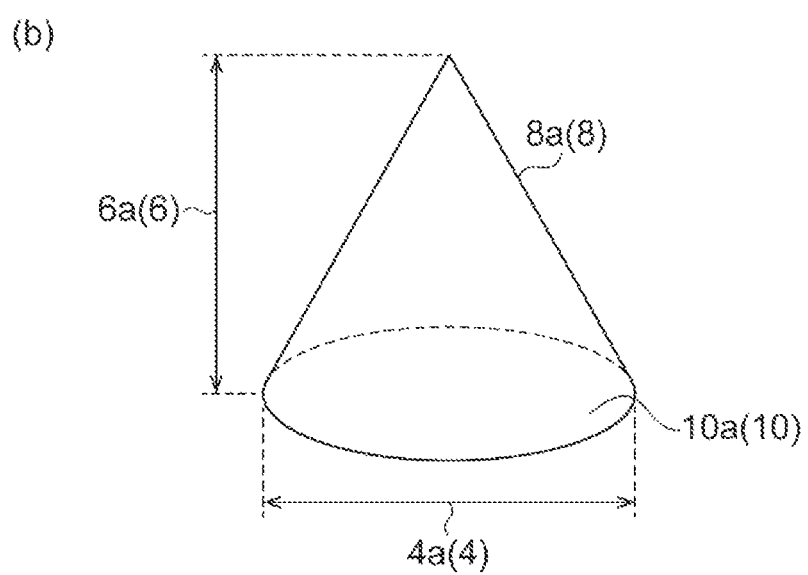
Figure 4:
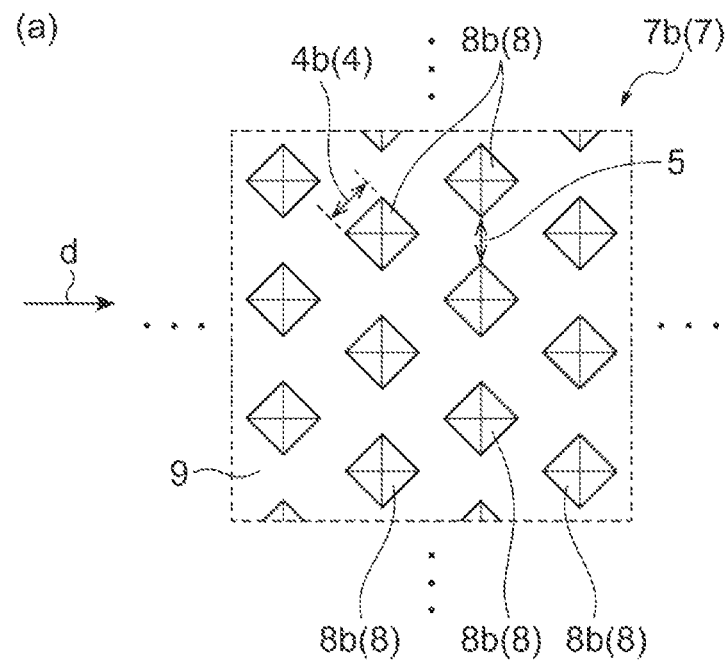
FIG. 4 shows (a) a plan view (top view) of a microstructure which is an embodiment of the present invention; and (b) a perspective view of a convex portion constituting the microstructure shown in (a).
Figure 4:
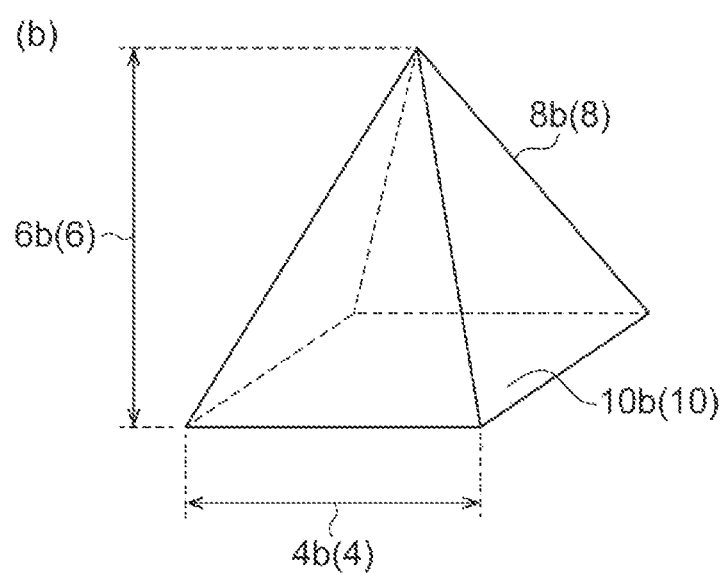
Figure 5:
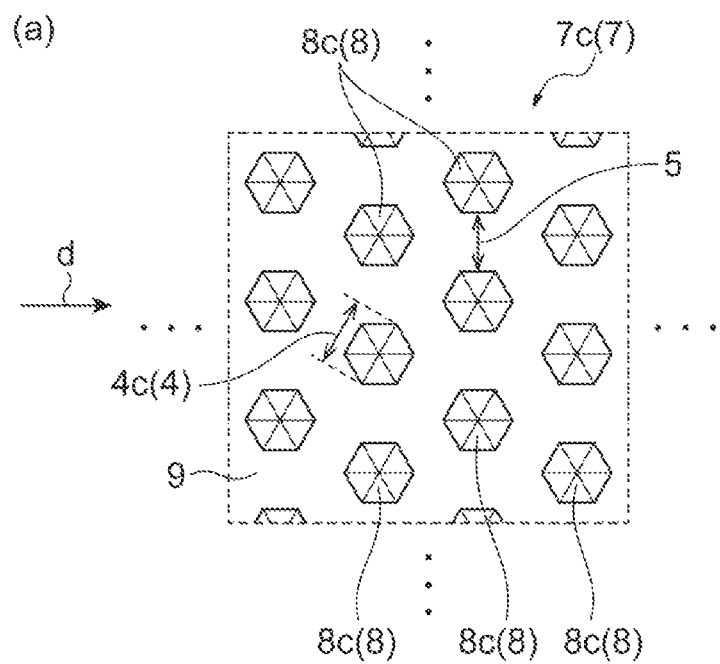
FIG. 5 shows (a) a plan view (top view) of a microstructure which is an embodiment of the present invention; and (b) a perspective view of a convex portion constituting the microstructure shown in (a).
Figure 5:
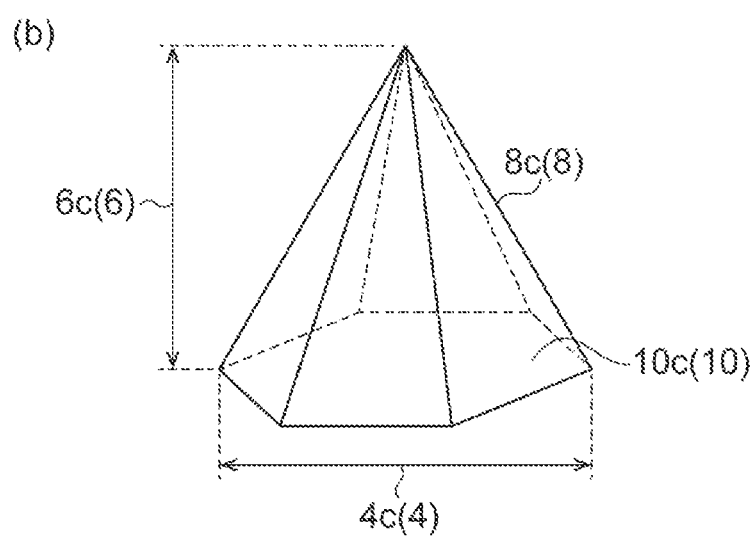
Figure 6:
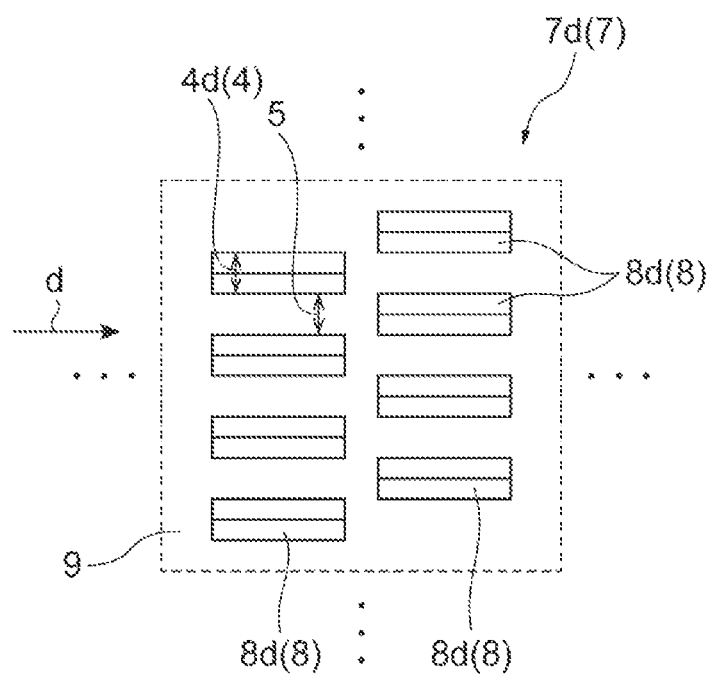
FIG. 6 shows (a) a plan view (top view) of a microstructure which is an embodiment of the present invention; and (b) a perspective view of a convex portion constituting the microstructure shown in (a).
Figure 6:
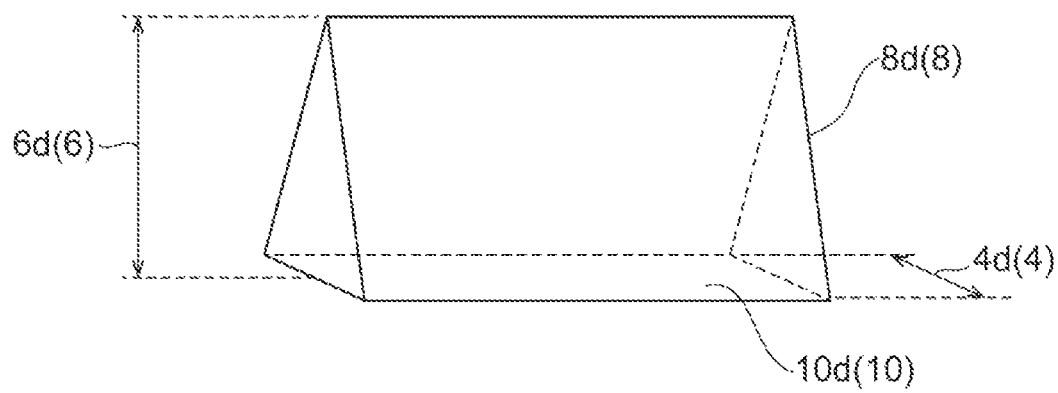

The shape of convex portions 8 constituting the microstructure 7 can be freely selected. Examples of the shape of the convex portions 8 include a cone, a polygonal pyramid, a truncated cone, a truncated polygonal pyramid, a cylinder, a polygonal column, a hemisphere and a semi-ellipsoid. For example, the shape of the convex portions 8a may be a cone as shown in FIG. 3. For example, the shape of the convex portions 8b may be a square pyramid as shown in FIG. 4. For example, the shape of the convex portions 8c may be a hexagonal pyramid as shown in FIG. 5. For example, the shape of the convex portions 8d may be a horizontally-long triangular prism (triangular prism placed such that a side surface of the triangular prism (a rectangular surface) is in contact with the flat part 9) as shown in FIG. 6. For the reasons that when the microstructure 7 is looked down (seen from the top) the entire surface of the membrane carrier 3 can be seen and a color change when a target substance is detected can be easily checked by an optical means, a cone structure such as a cone and polygonal pyramid is suitable as the shape of the convex portions 8, among the aforementioned shapes.

The shape of the convex portions 8 constituting the microstructure 7 is not necessary to be a geometrically accurate shape and may be a shape having a round corner and a shape having micro-convexoconcaves in the surface.

The diameter 4 of each of the bottom surfaces 10 of the convex portions 8 constituting the microstructure 7 may be 10 µm or more and 1000 µm or less and more preferably 15 µm or more and 1000 µm or less. The diameter 4 of the bottom surface 10 of the convex portion 8 may vary (be different from each other) among a plurality of convex portions 8 within the above range. If the diameter 4 of each of the bottom surfaces 10 of the convex portions 8 is 10 µm or more, the microfabrication cost of a mold for forming the microstructure 7 decreases and an infinite number of microstructure 7 can be easily and uniformly formed on the surface of the large-area membrane carrier 3. Accordingly, a microstructure constituted of the convex portions 8 having the bottom surface 10 of 10 µm or more in diameter 4, is more practical. If the diameter of each of the bottom surfaces 10 of the convex portions 8 is 10 µm or more, capillary force required for moving a liquid sample tends to increase. If the diameter 4 of each of the bottom surfaces 10 of the convex portions 8 is 1000 µm or less, the volume of metal scraped out from a metal member at the time of forming a mold can be reduced, with the result that fabrication costs for the mold and the membrane carrier 3 can be suppressed. If the diameter of each of the bottom surfaces 10 of the convex portions 8 is 1000 µm or less, the area of flow path 2 in the membrane carrier 3 can be reduced, with the result that a liquid sample test kit 18 can be miniaturized. This is advantageous for shipping the liquid sample test kit 18 itself.

The diameter 4 of each of the bottom surfaces 10 of the convex portions 8 is defined as the representative length of the bottom surface 10 of the convex portion 8. The representative length defining the bottom surface 10 is a diameter if the shape of the bottom surface 10 is a circle; the length of the shortest side if the shape is a triangle or a rectangle; the length of the longest diagonal line if the shape is a polygon of a pentagon or more; and a maximum length of the bottom surface 10 in the case of shapes except the aforementioned ones.

Figure 7:
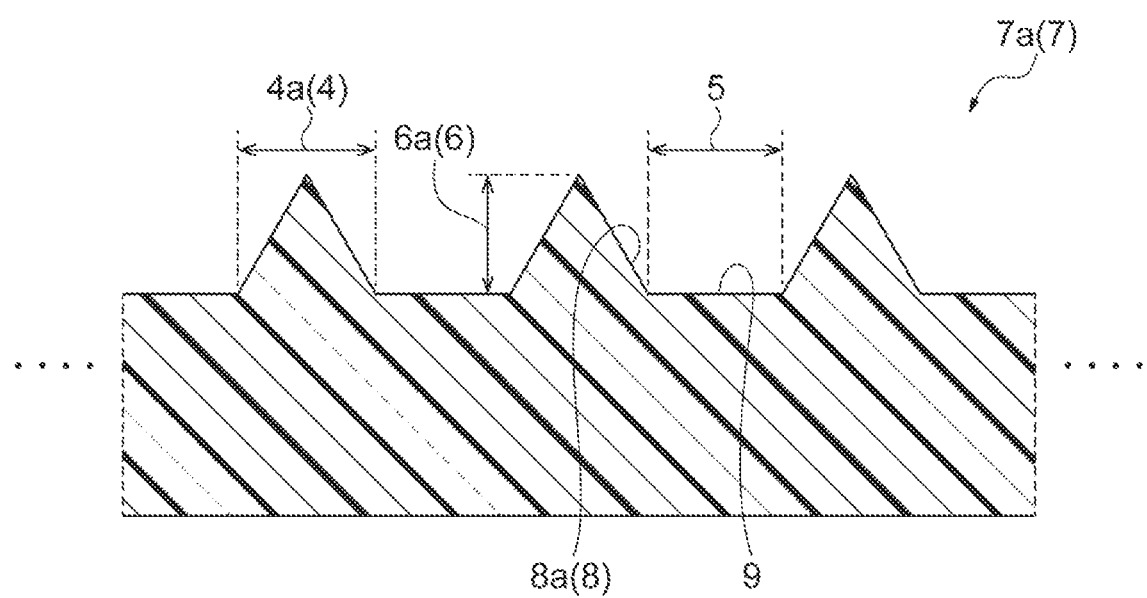
FIG. 7 shows a sectional view of a membrane carrier having a microstructure which is an embodiment of the present invention.

FIG. 7 is an aligned sectional view of the membrane carrier 3a having a microstructure 7a taken along the line VII-VII shown in FIG. 3. As shown in FIG. 3 and FIG. 7, if the shape of the convex portion 8a is a cone, the diameter 4a of the bottom surface 10a of the convex portion 8a corresponds to the diameter of the bottom (circle) of the cone. As shown in FIG. 4, if the shape of the convex portion 8b is a regular square pyramid, the diameter 4b of the bottom surface 10b of the convex portion 8b is the length of sides of the bottom surface (regular square) 10b. As shown in FIG. 5, if the shape of the convex portion 8c is a regular hexagonal pyramid, the diameter 4c of the bottom surface 10c of the convex portion 8c is the length of a diagonal line (length of the longest diagonal line) passing through the center of the bottom surface (regular hexagon) 10c. As shown in FIG. 6, if the shape of the convex portion 8d is a horizontally-long triangular prism, the diameter 4d of the bottom surface 10d of the convex portion 8d is the length of the shortest side of the bottom surface (rectangle) 10d (in FIG. 6, the length of the side perpendicular to the transport direction d of a liquid sample).

The height 6 of each of the convex portions 8 constituting the microstructure 7 is preferably 10 µm or more and 500 µm or less and more preferably 15 µm or more and 500 µm. The height 6 of the convex portions 8 may vary (be different from each other) among a plurality of convex portions 8 within the above range. If the height 6 of the convex portions 8 is 10 µm or more, the volume of the flow path 2 increases, with the result that a liquid sample can be developed in a shorter time. If the height 6 of each of the convex portions 8 is 500 µm or less, time and cost for forming the microstructure 7 can be reduced, with the result that it becomes easy to prepare the microstructure 7.

The height 6 of the convex portion 8 is defined as a maximum length of the convex portion 8 in the direction perpendicular to the flat part 9. As shown in FIG. 3 and FIG. 7, if the shape of the convex portion 8a is a cone, the height 6a of the convex portion 8a is a maximum length (the height of the cone) of the convex portion 8a in the direction perpendicular to the flat part 9. As shown in FIG. 4, if the shape of the convex portion 8b is a square pyramid, the height 6b of the convex portion 8b is a maximum length (the height of the square pyramid) of the convex portion 8b in the direction perpendicular to the flat part 9. As shown in FIG. 5, if the shape of the convex portion 8c is a hexagonal pyramid, the height 6c of the convex portion 8c is a maximum length (the height of the hexagonal pyramid) of the convex portion 8c in the direction perpendicular to the flat part 9. As shown in FIG. 6, if the shape of the convex portion 8d is a horizontally-long triangular prism, the height 6d of the convex portion 8d is a maximum length (the height of the horizontally-long triangular prism) of the convex portion 8d in the direction perpendicular to the flat part 9.

The bottom area (the area of a bottom surface 10 of the convex portion 8) of each of the convex portions 8 constituting the microstructure 7 is preferably 75 µm$^2$ or more and 250000 µm$^2$ or less. The bottom area of the convex portion 8 may vary (be different from each other) among a plurality of convex portions 8 within the above range. If the bottom area of the convex portion 8 is 78 µm$^2$ or more, microfabrication can be easily made, with the result that the manufacturing cost of the microstructure is further reduced. If the bottom area of the convex portion 8 is 250000 µm$^2$ or less, the number of convex portions 8 constituting the microstructure 7 within a single test kit increases, with the result that a liquid sample is more easily developed.

The nearest distance 5 between the convex portions 8 constituting the microstructure 7 is preferably 500 µm or less and more preferably 2 µm or more and 100 µm or less. The nearest distance 5 of the convex portion 8 may vary (be different from each other) among a plurality of convex portions 8 within the range. It is not conceivable that the nearest distance 5 between the convex portions 8 is less than 0 µm. If the nearest distance is 500 µm or less, the contact area between a liquid sample and the flow path 2 increases and thereby capillary force increases, with the result that a liquid sample can be more easily moved. The "nearest distance between the convex portions 8" herein refers to the nearest distance between a pair of adjacent convex portions 8 in the same region.

The aspect ratio of each of the convex portions 8 constituting the microstructure 7 is preferably 0.1 or more and 2.0 or less. The aspect ratio herein refers to a value obtained by dividing the height 6 (Lh) of the convex portion 8 by the representative length (diameter 4) (Lv) of the bottom surface 10 of the convex portion 8, (Lh/Lv). If the aspect ratio is 0.1 or more, the contact area between of a liquid sample and the flow path 2 increases and thereby capillary force increases, with the result that a liquid sample is more easily moved. If the aspect ratio is 2.0 or less, it becomes easy to prepare the microstructure.

The microstructure 7 may be constituted of the convex portions 8 mutually identical within the same region. The microstructure 7 may be constituted of the convex portions 8 mutually different within the same region. In this case, the mutually different convex portions 8 may be arranged along the transport direction d of a liquid sample in the same region in accordance with a predetermined rule. More specifically, the convex portions 8 may be arranged in the same region in such a way that at least one of for example, the diameter 4 of the bottom surface 10 of the convex portion 8, the height 6 of the convex portion 8, the nearest distance 5 between the convex portions 8 and the aspect ratio (Lh/Lv) of the convex portion 8 changes (increases or decreases) in the transport direction d of a liquid sample in accordance with the predetermined rule.

Figure 8:
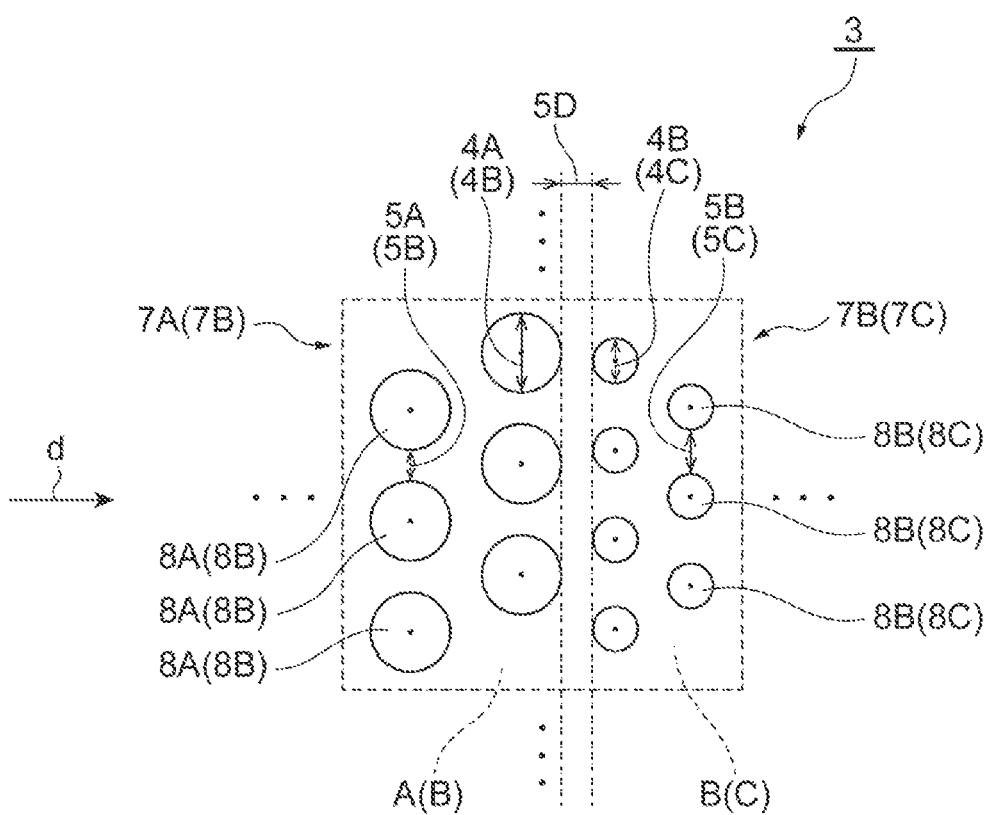
FIG. 8 shows an enlarged plan view (top view) of a site where microstructures change in a transport direction of a liquid sample which is an embodiment of the present invention.

FIG. 8 is an enlarged plan view (top view) of a site (near the boundary between first region A and second region B (or second region B and third region C) having mutually different microstructure) where the microstructure 7 changes along in the liquid sample transport direction. As shown in FIG. 8, first region A (second region B) and second region B (third region C) have mutually different microstructure 7A (7B) and 7B (7C). For example, if the microstructure 7A (7B) of first region A (second region B) is compared to the microstructure 7B (7C) of second region B (third region C), the convex portions 8A (8B) and 8B (8C) both have a conical shape, as shown in FIG. 3; however, the diameters 4A (4B) and 4B (4C) of the bottoms of the convex portions 8 mutually differ as well as the nearest distances 5A (5B) and 5B (5C) between the convex portions 8 within the same region mutually differ.

The microstructure 7A (7B) of first region A (second region B) and the microstructure 7B (7C) of second region B (third region C) may differ in at least one of, for example, the shape of the convex portion 8, the diameter 4 of the bottom surface 10 of the convex portion 8, the bottom area of the convex portion 8, the height 6 of the convex portion 8, the nearest distance 5 between the convex portions 8 in the same region and the aspect ratio (Lh/Lv) of the convex portion 8, other than in the example shown in FIG. 8.

The adjacent regions (first region A and second region B (or second region B and third region C)) are arranged at a predetermined interval between them. The nearest distance (also referred to as the buffer distance) 5D between the convex portions 8 mutually belonging to different regions is preferably 500 μm or less. The buffer distance 5D may be 1 μm or more. If the buffer distance 5D between the convex portions 8 is 500 μm or less, a liquid sample is more smoothly transported between the regions.

Since the membrane carrier 3 has the microstructure 7 mentioned above, the flow rate of a liquid sample flowing within the liquid sample test kit 18 (on the membrane carrier 3) changes along the transport direction d of a liquid sample. The flow rate in the liquid sample test kit 18 is evaluated based on the average flow rate in the region where the microstructure 7 is uniformly formed (first region A, second region B and third region C). The region where the microstructure 7 is uniformly formed refers to a region where identical microstructures 7 are arranged and a region where the microstructures 7 uniformly and continuously change in accordance with a predetermined rule. The average flow rate refers to a value obtained by dividing the distance (shortest distance) from the start point to the end point of the region where the microstructures 7 are uniformly formed in the direction of a liquid sample moving direction (transport direction d) by the time taken for the liquid sample to move (be transported) from the start point to the end point. The flow rate (average flow rate in each region) in the liquid sample test kit 18 can be measured by the method described later in Examples.

Figure 9:
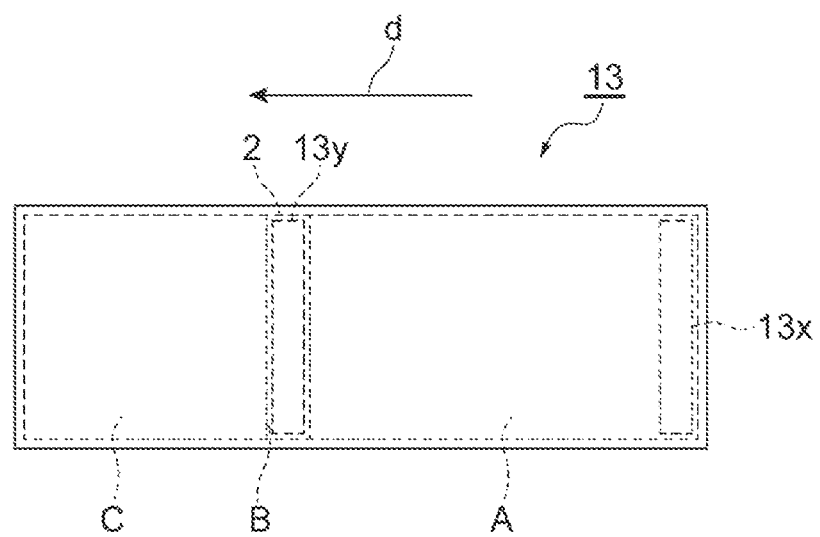
FIG. 9 shows a schematic top view showing a membrane which is an embodiment of the present invention.

FIG. 9 is a top view of a membrane carrier according to another embodiment. In the membrane carrier 3 shown in FIG. 2, a detection zone 3y is provided in third region C; whereas, in the membrane carrier 13 shown in FIG. 9, the detection zone 13y is provided in second region B. As shown in FIG. 9, the drop zone 13x and detection zone 13y may be formed over almost the entire shorter side of the membrane carrier 13.

The flow rate in second region B having the detection zone 13y is preferably slow compared to the flow rate in first region A having the drop zone 13x. In this case, the reactivity of a target substance with a detection substance becomes satisfactory and sensitivity of the test kit tends to be more improved. In this case, in order to reduce the test time by minimizing the length of second region B in the transport direction d where the flow rate is relatively slow, the length of second region B in the transport direction d in the membrane carrier 13, is set to be shorter than the length of first region A (further, third region C) in the transport direction d. The flow rate of third region C is preferably fast compared to the flow rate in second region B having the detection zone 13y. In this case, the time taken for a liquid sample to move (be transported) from the start point to the end point is more reduced. As a result, determination time can be reduced and, in addition, a reverse flow of a liquid sample from third region C (downstream region) to second region B having the detection zone 13y can be suppressed.

In the liquid sample test kit 18, the ratio of the largest flow rate to the smallest flow rate is preferably 1 or more and 10 or less. The ratio (of the largest flow rate to the smallest flow rate) is more preferably beyond 1.0 and 10 or less and further preferably 1.2 or more and 10 or less. It is not conceivable that the ratio (value) obtained by dividing the largest flow rate by the smallest flow rate is less than 1. If the value is 10 or less, spilling out of a liquid sample from the flow path 2 at a site where the flow-rate changes, and termination of development of the liquid sample are suppressed. The phrases "the smallest flow rate" and "the largest flow rate" respectively mean to the smallest average flow rate and the largest average flow rate of the average flow rates individually measured in a plurality of regions (first region A, second region B and third region C) provided in the membrane carrier 3.

The smallest flow rate and the largest flow rate in the liquid sample test kit 18 both are preferably 0.30 mm/s or more and 5.0 mm/s or less. If the smallest flow rate is 0.30 mm/s or more, occurrence of malfunction (for example, termination of liquid-sample development) caused by variability of test kits in production is further suppressed. If the largest flow rate is 5.0 mm/s or less, the flow of a liquid sample through the flow path 2 is more easily controlled and overflow of the liquid sample from the flow path 2 can be suppressed.

The microstructure 7 and the membrane carrier 3 of the liquid sample test kit 18 of the embodiment may be made of a thermoplastic. In other words, the membrane carrier 3 having the microstructure 7 can be produced by processing a film-like base material made of a thermoplastic. Examples of the processing method include thermal imprint, UV imprint, injection molding, etching, photolithography, machine cutting and laser processing. Of them, thermal imprint to a thermoplastic is suitable as a method for applying a precise processing at low cost. Examples of the thermoplastic include a polyester resin, a polyolefin resin, a polystyrene resin, a polycarbonate resin, a fluororesin and an acrylic resin. More specifically, various types of resins including polyethylene terephthalate (PET), a cycloolefin polymer (COP), polypropylene (PP), polystyrene (PS), polycarbonate (PC), polyvinylidene fluoride (PVDF) and polymethylmethacrylate (PMMA), can be used.

In the case of processing using a mold, such as imprint and injection molding, since the top of a cone is narrow compared to the bottom, the volume of metal scraped out in forming the mold is smaller than a columnar mold having the same bottom area, and thus, the mold can be prepared at low cost with a cone. In this case, a target substance in a liquid sample can be detected at low cost.

As described above, the membrane carrier 3, which is a membrane carrier 3 for the liquid sample test kit 18 for detecting a target substance in a liquid sample, has the microstructure 7 provided over the surface of the membrane carrier 3 and responsible for producing capillary action for transporting a liquid sample, and a flow path 2 formed of the microstructure 7 for transporting the liquid sample. In the membrane carrier 3, a plurality of regions A, B and C having the microstructure 7 and the flow path 2 are provided along the transport direction of a liquid sample. The adjacent regions A and B (B and C) have mutually different microstructures 7.

In the liquid sample test kit 18 according to the embodiment, a color change is produced in the detection zone 3y present in the membrane carrier 3, when a target substance is detected. The color change may be a color change observable by an optical means.

As the optical means, two methods: a visual determination means and means of measuring a fluorescence intensity, are mostly mentioned. In the case of visual determination, it is preferable to produce a color change expressed by a color difference ($\Delta E$ described in JIS Z8781-4:2013) of 0.5 or more between two color stimuli before and after detection when the color is measured by the color system of CIE1976L*a*b* color space. If the color difference is 0.5 or more, visually determination of color difference can be easily made. In the case of determination based on fluorescence-intensity measurement, it is preferable to produce a color difference satisfying a ratio of the fluorescence intensity (Fl1) in the detection zone 3y to the fluorescence intensity (Fl2) in upstream region and downstream region adjacent to the detection zone 3y, (Fl1/Fl2)=10/1 or more. If the ratio is 10/1 or more, signal and noise can be easily separated.

To prepare the detection zone 3y in the liquid sample test kit 18 of the embodiment, a detection substance is immobilized in at least part of the flow path 2, in an embodiment. More specifically, a detection substance detecting a target substance is immobilized in the detection zone 3y. A color change in the detection zone 3y is produced by holding a target substance by the detection substance (through reaction with the detection substance) in the detection zone 3y.

In other words, a method for producing the liquid sample test kit 18 comprises a step of immobilizing, to the detection zone 3y, a detection substance which produces a color change by holding the target substance in the detection zone 3y. For the reason that a detection substance (reagent) can be efficiently immobilized in the detection zone 3y, the surface treatment may be previously applied to the site of the membrane carrier 3, at which the detection zone 3y is to be provided.

The surface treatment method is not limited and, for example, various methods such as UV irradiation, a UV/ozone treatment, various plasma treatments and surface modification with, for example, 3-aminopropyltriethoxysilane or glutaraldehyde, can be used.

In the embodiment, as the detection substance (reagent), for example, an antibody is mentioned. The antibody is an antibody which binds to a target substance through an antigen-antibody reaction, and may be a polyclonal antibody or a monoclonal antibody.

The color change in the detection zone 3y may be produced by a label having an antibody or an antigen-binding fragment thereof specifically reacting with a target substance in a liquid sample. The color change is produced by, for example, holding a label by a detection substance (through a reaction with (binding to) the detection substance) in the detection zone 3y and producing a color.

The label is, for example, a label in which an antibody or an antigen-binding fragment thereof is bound to particles such as colloidal particles and latex particles. The antigen-binding fragment refers to a fragment specifically binding to a target substance, such as an antigen-binding fragment of an antibody. The label can bind to a target substance via an antibody or an antigen-binding fragment thereof. The particles may have magnetic property or fluorogenicity. Examples of the colloidal particles include metallic colloidal particles such as gold colloidal particles and platinum colloidal particles. The particles are preferably latex particles in view of control of particle size, dispersion stability and binding ability. The material for latex particles is not particularly limited; however, polystyrene is preferable.

In view of visibility, the particles are preferably colored particles or fluorescent particles and more preferably colored particles. The colored particles are satisfactory if the color thereof is detectable by the naked eye. The fluorescent particles are satisfactory if they contain a fluorescence substance. The particles may be colored latex particles or fluorescent latex particles. If the particles are colored latex particles, the color change mentioned above is suitably detected visually. If the particles are fluorescent latex particles, the color change mentioned above is suitably detected by fluorescence-intensity measurement.

In order for the label as mentioned above to successfully react with a target substance in a liquid sample to be delivered dropwise, the label is provided to at least a part of the test kit 18. The label may be provided, for example, to a member in the test kit 18 or may be provided to at least a part (upstream the detection zone 3y) of the flow path 2 of the membrane carrier 3. The label reacted with (bound to) a target substance is held by a detection substance (through reaction (binding) of the detection substance with the target substance) in the detection zone 3y. In this manner, a color change (color produced by a label) is produced in the detection zone 3y.

A method for testing a liquid sample according to one aspect of the embodiment is a test method using the test kit 18.

The method for testing a liquid sample using the test kit 18 may comprise a step of preparing a mixed liquid sample by mixing the liquid sample and a label specifically binding to a target substance in the liquid sample to mutually bind the target substance and the label; a step of delivering a drop of the mixed liquid sample to the drop zone 3x provided in the membrane carrier 3; a step of transporting the mixed liquid sample from the drop zone 3x to the detection zone 3y through the microstructure 7; and a step of detecting a color change (color of label) in the detection zone 3y.

Alternatively, the above test method may comprise a step of delivering a drop of a liquid sample to the drop zone 3x in the surface of the membrane carrier 3; a step of transporting the liquid sample from the drop zone 3x to the detection zone 3y through the microstructure 7 with the help of capillary action exerted by the microstructure 7 (convex portions 8) formed on the surface of the membrane carrier 3; and a step of binding a target substance in a liquid sample to the label via the antibody or an antigen-binding fragment thereof, further, binding the target substance to a reagent immobilized in the detection zone 3y and detecting a color change in the detection zone 3y (optically determining the presence or absence of color change).

In the step of mutually binding a target substance and a label in the above test method, a method for mixing a liquid sample and the label is not particularly limited. For example, a method of adding a liquid sample in a container containing the label or a method of mixing a liquid containing, for example, a label, and a liquid sample may be employed. Alternatively, a filter is inserted in a drip opening of a container containing, for example, a liquid sample, and a label may be immobilized in the filter.

EXAMPLES

The embodiments will be described, however, the embodiments are not limited by these Experimental Examples.

Experimental Example 1

<Preparation of Mold>

The mold was prepared by laser processing and machine cutting. FIG. 10 shows a mold 20 for forming a microstructure. The mold 20 shown in FIG. 10 has a plurality of regions (first region A, second region B and third region C) and concave portions corresponding to the convex portions of the microstructure shown in FIG. 8 are formed in the surface thereof (not shown). The mold 20 is made of aluminum alloy A5052. At the center portion of the mold within the range of 30 mm×30 mm, microfabrication is applied. In the fabrication range of the mold 20, the region (region A) within the fabrication range at a distance 16 mm inward a predetermined side (20A) and the region (region C), within the fabrication range at a distance of 11 mm inward from the opposite side (20B) to the predetermined side, cone-shape concave portions of 10 μm in diameter and 10 μm in depth (in Tables, sometimes referred to as height) are arranged at the nearest distance between microstructures (5A, 5C) of 5 μm in a staggered arrangement, as shown in FIG. 8. In the range (region B) other than the above fabrication ranges, cone-shape concave portions of 10 μm in diameter and 10 μm in depth are arranged at the nearest distance between microstructures (5B) of 5 μm in a staggered arrangement as shown in FIG. 8. Note that, the buffer distance 5D between regions A and B and the buffer distance 5D between regions B and C are both 5 μm.

In order to easily separate the mold and a thermoplastic without fail at the time of transfer printing, a release treatment was applied to the convex-concave surface of the mold. The release treatment was applied by soaking the mold in Optool HD-2100TH manufactured by Daikin Industries Ltd. for about one minute, drying and allowing the mold to stand still overnight.

<Transfer Printing of Microstructure>

Using the mold obtained as mentioned above, the microstructure was transfer-printed to a thermoplastic. As the thermoplastic, polystyrene (Denka styrene sheet manufactured by Denka Company Limited, film thickness 300 μm) was used. As the processing method, thermal imprint was used. As the apparatus, X-300 manufactured by SCIVAX was used. Transfer printing was carried out at a molding temperature of 120° C. and an applied pressure of 5.5 MPa for 10 minutes. After the transfer-printing, the thermoplastic and the mold were cooled up to 80° C. while applying the pressure, and then, the pressure was eliminated to prepare a membrane carrier having region A, region B and region C in this order from one end.

Experimental Example 2

A membrane carrier was prepared in the same conditions as in Experimental Example 1 except that as cone-shape concave portions having a diameter of 100 μm and a depth 100 μm were used in place of the microstructures of regions A, B and C of Experimental Example 1.

Experimental Example 3

A membrane carrier was prepared in the same conditions as in Experimental Example 1 except that cone-shape concave portions having a diameter of 500 μm and a depth 500 μm were used in place of the microstructures of regions A, B and C of Experimental Example 1.

Experimental Example 4

A membrane carrier was prepared in the same conditions as in Experimental Example 1 except that cone-shape concave portions having a diameter of 100 μm and a depth 100 μm were used in place of the microstructures of regions A and C and cone-shape concave portions having a diameter of 30 μm and a depth 30 μm were used in place of the microstructures of region B of Experimental Example 1.

Experimental Example 5

A membrane carrier was prepared in the same conditions as in Experimental Example 1 except that cone-shape concave portions having a diameter of 250 μm and a depth 250 μm were used in place of the microstructures of regions A and C of Experimental Example 4 and cone-shape concave portions having a diameter of 30 μm and a depth 30 μm were used in place of the microstructures of region B of Experimental Example 4.

Experimental Example 6

A membrane carrier was prepared in the same conditions as in Experimental Example 1 except that cone-shape concave portions having a diameter of 250 μm and a depth 250 μm were used in place of the microstructures of regions A and C of Experimental Example 4 and cone-shape concave portions having a diameter of 10 μm and a depth 10 μm were used in place of the microstructures of region B of Experimental Example 4.

Experimental Example 7

A membrane carrier was prepared in the same conditions as in Experimental Example 1 except that cone-shape concave portions having a diameter of 100 μm and a depth 100 μm were used in place of the microstructures of regions A and C of Experimental Example 4 and cone-shape concave portions having a diameter of 10 μm and a depth 10 μm were used in place of the microstructures of region B of Experimental Example 4.

Experimental Example 8

A membrane carrier was prepared in the same conditions as in Experimental Example 1 except that cone-shape concave portions having a diameter of 500 μm and a depth 500 μm were used in place of the microstructures of regions A and C of Experimental Example 4 and cone-shape concave portions having a diameter of 10 μm and a depth 10 μm were used in place of the microstructures of region B of Experimental Example 4.

Experimental Example 9

A membrane carrier was prepared in the same conditions as in Experimental Example 1 except that the microstructures of region A in Experimental Example 4 were divided into 16 compartments having a width of 1 mm in the direction perpendicular to the transport direction in such a manner that the diameter and depth of the cone-shape concave portions serially reduced as a unit of compartment by 4.7 µm from 100 µm toward region B (serially reduced by 4.7 µm from 100 µm along the transport direction); and that the microstructures of region C in Experimental Example 4 were divided into 11 compartments having a width of 1 mm in the direction perpendicular to the transport direction in such a manner that the diameter and depth of the cone-shape concave portions serially reduced as a unit of compartment by 7 µm from 100 µm toward region B (serially increased by 7 µm from 100 µm along the transport direction).

Example 10

A membrane carrier was prepared in the same conditions as in Experimental Example 1 except that the microstructures of region A in Experimental Example 4 were divided into 16 compartments having a width of 1 mm in the direction perpendicular to the transport direction in such a manner that the diameter and depth of the cone-shape concave portions serially reduced as a unit of compartment by 14.7 µm from 250 µm toward region B; and that the microstructures of region C in Experimental Example 4 were divided into 11 compartments having a width of 1 mm in the direction perpendicular to the transport direction in such a manner that the diameter and depth of the cone-shape concave portions serially reduced as a unit of compartment by 22 µm from 250 µm toward region B.

Experimental Example 11

A membrane carrier was prepared in the same conditions as in Experimental Example 1 except that the microstructures of regions A and C were specified to have a diameter of 50 µm and the microstructures of region B was specified to have a diameter of 15 µm in Experimental Example 4.

Experimental Example 12

A membrane carrier was prepared in the same conditions as in Experimental Example 1 except that the microstructures of regions A and C were specified to have a diameter of 50 µm and the microstructures of region B was specified to have a diameter of 300 µm in Experimental Example 4.

Experimental Example 13

A membrane carrier was prepared in the same conditions as in Experimental Example 1 except that the microstructures of regions A and C were specified to have a diameter of 500 µm and the microstructures of region B was specified to have a diameter of 300 µm in Experimental Example 4.

Experimental Example 14

A membrane carrier was prepared in the same conditions as in Experimental Example 1 except that the microstructures of region B were specified as cone-shape concave portions having a diameter of 200 µm and a depth of 100 µm in Experimental Example 4.

Experimental Example 15

A membrane carrier was prepared in the same conditions as in Experimental Example 1 except that the microstructures of region B were specified as cone-shape concave portions having a diameter of 500 µm and a depth of 100 µm in Experimental Example 4.

Experimental Example 16

A membrane carrier was prepared in the same conditions as in Experimental Example 1 except that the microstructures of region A in Experimental Example 4 were divided into 16 compartments having a width of 1 mm in the direction perpendicular to the transport direction in such a manner that the diameter of the cone-shape concave portions serially increased as a unit of compartment by 10 µm from 100 µm toward region B; that the microstructures of region C in Experimental Example 4 were divided into 11 compartments having a width of 1 mm in the direction perpendicular to the transport direction in such a manner that the diameter of the cone-shape concave portions serially increased as a unit of compartment by 15 µm from 100 µm toward region B; and that the cone-shape concave portions in region B were specified to have a diameter of 250 µm and a depth 100 µm.

Experimental Example 17

A membrane carrier was prepared in the same conditions as in Experimental Example 1 except that the microstructures of region A in Experimental Example 4 were divided into 16 compartments having a width of 1 mm in the direction perpendicular to the transport direction in such a manner that the diameter of the cone-shape concave portions serially increased as a unit of compartment by 26.7 µm from 100 µm toward region B; that the microstructures of region C in Experimental Example 4 were divided into 11 compartments having a width of 1 mm in such a manner that the diameter of the cone-shape concave portions serially increased as a unit of compartment by 40 µm from 100 µm toward region B; and that the cone-shape concave portions in region B were specified to have a diameter of 500 µm and a depth 100 µm.

Experimental Example 18

A membrane carrier was prepared in the same conditions as in Experimental Example 1 except that the microstructures of region B were specified as cone-shape concave portions having a diameter of 100 µm and a depth of 100 µm and the nearest distance between the microstructures was specified as 30 µm in Experimental Example 4.

Experimental Example 19

A membrane carrier was prepared in the same conditions as in Experimental Example 1 except that the microstructures of region B were specified as cone-shape concave portions having a diameter of 100 µm and a depth of 100 µm and the nearest distance between the microstructures was specified as 100 µm in Experimental Example 4.

Experimental Example 20

A membrane carrier was prepared in the same conditions as in Experimental Example 1 except that the microstructures of regions A and C in Experimental Example 4 were specified as cone-shape concave portions having a diameter of 500 µm and a depth of 500 µm; that the microstructures of region B in Experimental Example 4 were specified as cone-shape concave portions having a diameter of 500 µm and a depth of 500 µm; and that the nearest distance between the microstructures was specified as 100 µm.

Experimental Example 21

A membrane carrier was prepared in the same conditions as in Experimental Example 1 except that the microstructures of regions A and C in Experimental Example 4 were specified as cone-shape concave portions having a diameter of 500 μm and a depth of 500 μm; that the microstructures of region B in Experimental Example 4 were specified as cone-shape concave portions having a diameter of 500 μm and a depth of 500 μm; and that the nearest distance between the microstructures was specified as 500 μm.

Experimental Example 22

A membrane carrier was prepared in the same conditions as in Experimental Example 1 except that the microstructures of regions A and C in Experimental Example 4 were specified as cone-shape concave portions having a diameter of 250 μm and a depth of 250 μm; that the microstructures of region B in Experimental Example 4 were specified as cone-shape concave portions having a diameter of 250 μm and a depth of 250 μm; and that the nearest distance between the microstructures was specified as 100 μm.

Experimental Example 23

A membrane carrier was prepared in the same conditions as in Experimental Example 1 except that the microstructures of regions A and C in Experimental Example 4 were specified as cone-shape concave portions having a diameter of 250 μm and a depth of 250 μm; that the microstructures of region B in Experimental Example 4 were specified as cone-shape concave portions having a diameter of 250 μm and a depth of 250 μm; and that the nearest distance between the microstructures was specified as 250 μm.

Experimental Example 24

A membrane carrier was prepared in the same conditions as in Experimental Example 1 except that the microstructures of region A in Experimental Example 4 were divided into 16 compartments having a width of 1 mm in the direction perpendicular to the transport direction in such a manner that the nearest distance between microstructures serially increased as a unit of compartment by 1.7 μm from 5 μm toward region B; that the microstructures of region C in Experimental Example 4 were divided into 11 compartments having a width of 1 mm in the direction perpendicular to the transport direction in such a manner that the nearest distance between microstructures serially increased as a unit of compartment by 2.5 μm from 5 μm toward region B; and that the microstructures of region B were specified as cone-shape concave portions having a diameter of 100 μm and a depth 100 μm and the nearest distance between microstructures was 30 μm.

<Preparation of Detection Zone>

UV treatment was applied only to a portion of a membrane carrier prepared as mentioned above and having the structure of region B transfer-printed. To the portion, an anti-type A influenza NP antibody suspension solution and an anti-type B influenza NP antibody suspension solution each were applied in a line width of 1 mm (coating amounts each were 3 μL) and sufficiently dried by hot air to immobilize the detection substances.

<Preparation of Label>

A purified anti-type A influenza virus NP antibody (another antibody as used in the above) and a purified anti-type B influenza virus NP antibody (another antibody as used in the above) were used. The anti-type A influenza virus NP antibody was covalently labeled with blue latex particles (CM/BL made from Ceradyne Inc.) having a particle size of 0.394 μm, suspended in a Tris buffer solution containing a sugar, a surfactant and a protein such that the concentration of the latex particles became 0.025 w/v %, and ultrasonically treated to prepare an anti-type A label sufficiently dispersed and suspended. Anti-type B label was similarly prepared by labeling an anti-type B influenza virus NP antibody with blue latex particles.

The anti-type A label and the anti-type B label were mixed and applied to the glass fiber having a size of 3 cm×1 cm (33GLASS No. 10539766, manufactured by Schleicher & Schuell) in an amount of 50 μL per square centimeter and dried well by hot air to produce a label pad. Thereafter, the label pad was overlapped with the edge portion (just by 2 mm) of region A of each of the membrane carriers produced in accordance with Experimental Examples 1 to 24 and cut into strips having a width of 5 mm by a cutter to prepare integrated liquid sample test kits.

<Detection Evaluation>

On the label pad (drop zone) of the edge of the liquid sample test kit prepared as mentioned above, the liquid sample (100 μL) was dropped. As the liquid sample, two types of samples were used; one is a type A influenza virus, A/Beijing/32/92 (H3N2) solution diluted with a specimen suspension solution attached to Quick navi-Flu manufactured by Denka Seiken Co., Ltd. as a dilution solution, up to $4 \times 10^4$ fold, and the other is a type B influenza virus B/Shangdong/7/97 solution diluted up to $4 \times 10^3$ fold. After dropwise addition, behavior of (how to move) the liquid sample was videotaped above the sample, by a digital camera. From the videotape, the flow rate of the liquid sample moving in each of regions A to C was evaluated. As the flow rate, an average value (average flow rate) of the flow rate of the diluted type A influenza virus solution and the flow rate of the diluted type B influenza virus solution, was used. A flow-rate ratio was obtained by dividing the largest flow rate by the smallest flow rate. The results were shown in Tables 1 to 3.

TABLE 1

| | Experimental Example 1 | Experimental Example 2 | Experimental Example 3 | Experimental Example 4 | Experimental Example 5 |
|---|---|---|---|---|---|
| Nearest distance (μm) between microstructures (convex portions) in region A | 5 | 5 | 5 | 5 | 5 |
| Nearest distance (μm) between microstructures (convex portions) in region B | 5 | 5 | 5 | 5 | 5 |

TABLE 1-continued

|  | | | | | |
|---|---|---|---|---|---|
| Nearest distance (μm) between microstructures (convex portions) in region C | 5 | 5 | 5 | 5 | 5 |
| Diameter (μm) of convex portions in region A | 10 | 100 | 500 | 100 | 250 |
| Height (μm) of convex portions in region A | 10 | 100 | 500 | 100 | 250 |
| Diameter (μm) of convex portions in region B | 10 | 100 | 500 | 30 | 30 |
| Height (μm) of convex portions in region B | 10 | 100 | 500 | 30 | 30 |
| Diameter (μm) of convex portions in region C | 10 | 100 | 500 | 100 | 250 |
| Height (μm) of convex portions in region C | 10 | 100 | 500 | 100 | 250 |
| Aspect ratio | 1 | 1 | 1 | 1 | 1 |
| Average flow rate (mm/s) in region A | 1.2 | 3.2 | 3.5 | 3.2 | 3.5 |
| Average flow rate (mm/s) in region B | 1.2 | 3.2 | 3.5 | 2.5 | 2.5 |
| Average flow rate (mm/s) in region C | 1.2 | 3.2 | 3.5 | 3.2 | 3.5 |
| Flow-rate ratio | 1.0 | 1.0 | 1.0 | 1.3 | 1.4 |
| Maximum visible-determination allowable dilution rate of type A | $5 \times 10^4$ | $4 \times 10^4$ | $2 \times 10^4$ | $5 \times 10^4$ | $5 \times 10^4$ |
| Maximum visible-determination allowable dilution rate of type B | $5 \times 10^3$ | $4 \times 10^3$ | $2 \times 10^3$ | $5 \times 10^3$ | $5 \times 10^3$ |
| Time (minutes) until concentration becomes stable | 7 | 4 | 4 | 4 | 4 |
| Overall evaluation | C | C | C | A | A |
| Note | Reference Example | Reference Example | Reference Example | Example | Example |

|  | Experimental Example 6 | Experimental Example 7 | Experimental Example 8 | Experimental Example 9 | Experimental Example 10 |
|---|---|---|---|---|---|
| Nearest distance (μm) between microstructures (convex portions) in region A | 5 | 5 | 5 | 5 | 5 |
| Nearest distance (μm) between microstructures (convex portions) in region B | 5 | 5 | 5 | 5 | 5 |
| Nearest distance (μm) between microstructures (convex portions) in region C | 5 | 5 | 5 | 5 | 5 |
| Diameter (μm) of convex portions in region A | 250 | 100 | 500 | Serially reduced by 4.7 from 100 | Serially reduced by 14.7 from 250 |
| Height (μm) of convex portions in region A | 250 | 100 | 500 | Serially reduced by 4.7 from 100 | Serially reduced by 14.7 from 250 |
| Diameter (μm) of convex portions in region B | 10 | 10 | 10 | 30 | 30 |
| Height (μm) of convex portions in region B | 10 | 10 | 10 | 30 | 30 |
| Diameter (μm) of convex portions in region C | 250 | 100 | 500 | Serially reduced by 7 from 100 | Serially reduced by 22 from 250 |
| Height (μm) of convex portions in region C | 250 | 100 | 500 | Serially reduced by 7 from 100 | Serially reduced by 22 from 250 |
| Aspect ratio | 1 | 1 | 1 | 1 | 1 |
| Average flow rate (mm/s) in region A | 3.5 | 3.2 | 3.7 | 3.0 | 3.2 |
| Average flow rate (mm/s) in region B | 1.2 | 1.2 | 1.2 | 2.5 | 2.5 |
| Average flow rate (mm/s) in region C | 3.5 | 3.2 | 3.7 | 2.7 | 3.0 |
| Flow-rate ratio | 2.9 | 2.7 | 3.1 | 1.2 | 1.3 |
| Maximum visible-determination allowable dilution rate of type A | $6 \times 10^4$ | $6 \times 10^4$ | $6 \times 10^4$ | $5 \times 10^4$ | $5 \times 10^4$ |

TABLE 1-continued

|  |  |  |  |  |  |
| --- | --- | --- | --- | --- | --- |
| Maximum visible-determination allowable dilution rate of type B | $6 \times 10^3$ | $6 \times 10^3$ | $6 \times 10^3$ | $5 \times 10^3$ | $5 \times 10^3$ |
| Time (minutes) until concentration becomes stable | 5 | 5 | 5 | 4 | 4 |
| Overall evaluation | B | B | B | A | A |
| Note | Example | Example | Example | Example | Example |

TABLE 2

|  | Experimental Example 11 | Experimental Example 12 | Experimental Example 13 |
| --- | --- | --- | --- |
| Nearest distance (μm) between microstructures (convex portions) in region A | 5 | 5 | 5 |
| Nearest distance (μm) between microstructures (convex portions) in region B | 5 | 5 | 5 |
| Nearest distance (μm) between microstructures (convex portions) in region C | 5 | 5 | 5 |
| Diameter (μm) of convex portions in region A | 50 | 50 | 500 |
| Height (μm) of convex portions in region A | 100 | 100 | 100 |
| Diameter (μm) of convex portions in region B | 15 | 300 | 300 |
| Height (μm) of convex portions in region B | 30 | 30 | 30 |
| Diameter (μm) of convex portions in region C | 50 | 50 | 500 |
| Height (μm) of convex portions in region C | 100 | 100 | 100 |
| Aspect ratio | 2 | 0.1-2 | 0.1-0.2 |
| Average flow rate (mm/s) in region A | 3.6 | 3.7 | 3.0 |
| Average flow rate (mm/s) in region B | 2.7 | 1.3 | 1.3 |
| Average flow rate (mm/s) in region C | 3.6 | 3.7 | 3.0 |
| Flow-rate ratio | 1.3 | 2.8 | 2.3 |
| Maximum visible-determination allowable dilution rate of type A | $5 \times 10^4$ | $6 \times 10^4$ | $6 \times 10^4$ |
| Maximum visible-determination allowable dilution rate of type B | $5 \times 10^3$ | $6 \times 10^3$ | $6 \times 10^3$ |
| Time (minutes) until concentration becomes stable | 4 | 5 | 5 |
| Overall evaluation | A | B | B |
| Note | Example | Example | Example |

|  | Experimental Example 14 | Experimental Example 15 | Experimental Example 16 | Experimental Example 17 |
| --- | --- | --- | --- | --- |
| Nearest distance (μm) between microstructures (convex portions) in region A | 5 | 5 | 5 | 5 |
| Nearest distance (μm) between microstructures (convex portions) in region B | 5 | 5 | 5 | 5 |
| Nearest distance (μm) between microstructures (convex portions) in region C | 5 | 5 | 5 | 5 |
| Diameter (μm) of convex portions in region A | 100 | 100 | Serially increased by 10 from 100 | Serially increased by 26.7 from 100 |
| Height (μm) of convex portions in region A | 100 | 100 | 100 | 100 |
| Diameter (μm) of convex portions in region B | 200 | 500 | 250 | 500 |
| Height (μm) of convex portions in region B | 100 | 100 | 100 | 100 |
| Diameter (μm) of convex portions in region C | 100 | 100 | Serially increased by 15 from 100 | Serially increased by 40 from 100 |
| Height (μm) of convex portions in region C | 100 | 100 | 100 | 100 |
| Aspect ratio | 0.5-1 | 0.2-1 | 0.4-1 | 0.2-1 |
| Average flow rate (mm/s) in region A | 3.2 | 3.2 | 3.0 | 2.9 |
| Average flow rate (mm/s) in region B | 2.4 | 2.0 | 2.8 | 2.4 |
| Average flow rate (mm/s) in region C | 3.2 | 3.2 | 2.9 | 2.7 |
| Flow-rate ratio | 1.3 | 1.6 | 1.1 | 1.2 |
| Maximum visible-determination allowable dilution rate of type A | $5 \times 10^4$ | $5 \times 10^4$ | $5 \times 10^4$ | $5 \times 10^4$ |
| Maximum visible-determination allowable dilution rate of type B | $5 \times 10^3$ | $5 \times 10^3$ | $5 \times 10^3$ | $5 \times 10^3$ |

TABLE 2-continued

| | | | | |
|---|---|---|---|---|
| Time (minutes) until concentration becomes stable | 4 | 4 | 4 | 5 |
| Overall evaluation | A | A | A | B |
| Note | Example | Example | Example | Example |

TABLE 3

| | Experimental Example 18 | Experimental Example 19 | Experimental Example 20 | Experimental Example 21 |
|---|---|---|---|---|
| Nearest distance (μm) between microstructures (convex portions) in region A | 5 | 5 | 5 | 5 |
| Nearest distance (μm) between microstructures (convex portions) in region B | 30 | 100 | 100 | 500 |
| Nearest distance (μm) between microstructures (convex portions) in region C | 5 | 5 | 5 | 5 |
| Diameter (μm) of convex portions in region A | 100 | 100 | 500 | 500 |
| Height (μm) of convex portions in region A | 100 | 100 | 500 | 500 |
| Diameter (μm) of convex portions in region B | 100 | 100 | 500 | 500 |
| Height (μm) of convex portions in region B | 100 | 100 | 500 | 500 |
| Diameter (μm) of convex portions in region C | 100 | 100 | 500 | 500 |
| Height (μm) of convex portions in region C | 100 | 100 | 500 | 500 |
| Aspect ratio | 1 | 1 | 1 | 1 |
| Average flow rate (mm/s) in region A | 3.2 | 3.2 | 3.7 | 3.7 |
| Average flow rate (mm/s) in region B | 1.0 | 0.33 | 1.5 | 0.37 |
| Average flow rate (mm/s) in region C | 3.2 | 3.2 | 3.7 | 3.7 |
| Flow-rate ratio | 3.2 | 9.7 | 2.5 | 10.0 |
| Maximum visible-determination allowable dilution rate of type A | $6 \times 10^4$ | $7 \times 10^4$ | $5 \times 10^4$ | $7 \times 10^4$ |
| Maximum visible-determination allowable dilution rate of type B | $6 \times 10^3$ | $7 \times 10^3$ | $5 \times 10^3$ | $7 \times 10^3$ |
| Time (minutes) until concentration becomes stable | 5 | 6 | 5 | 6 |
| Overall evaluation | B | A | B | A |
| Note | Example | Example | Example | Example |

| | Experimental Example 22 | Experimental Example 23 | Experimental Example 24 |
|---|---|---|---|
| Nearest distance (μm) between microstructures (convex portions) in region A | 5 | 5 | Serially increased by 1.7 from 5 |
| Nearest distance (μm) between microstructures (convex portions) in region B | 100 | 250 | 30 |
| Nearest distance (μm) between microstructures (convex portions) in region C | 5 | 5 | Serially increased by 2.5 from 5 |
| Diameter (μm) of convex portions in region A | 250 | 250 | 100 |
| Height (μm) of convex portions in region A | 250 | 250 | 100 |
| Diameter (μm) of convex portions in region B | 250 | 250 | 100 |
| Height (μm) of convex portions in region B | 250 | 250 | 100 |
| Diameter (μm) of convex portions in region C | 250 | 250 | 100 |
| Height (μm) of convex portions in region C | 250 | 250 | 100 |
| Aspect ratio | 1 | 1 | 1 |
| Average flow rate (mm/s) in region A | 3.5 | 3.5 | 2.5 |
| Average flow rate (mm/s) in region B | 0.40 | 0.35 | 1.0 |
| Average flow rate (mm/s) in region C | 3.5 | 3.5 | 2.1 |
| Flow-rate ratio | 8.8 | 10.0 | 2.5 |
| Maximum visible-determination allowable dilution rate of type A | $7 \times 10^4$ | $7 \times 10^4$ | $6 \times 10^4$ |
| Maximum visible-determination allowable dilution rate of type B | $7 \times 10^3$ | $7 \times 10^3$ | $6 \times 10^3$ |
| Time (minutes) until concentration becomes stable | 6 | 6 | 6 |
| Overall evaluation | A | A | B |
| Note | Example | Example | Example |

Determination of detection was made by visually observing the presence or absence of a color line in the detection zones (A influenza virus detection section and B influenza virus detection section) 15 minutes later.

As a result of determination, in the case of using the A/Beijing/32/92 (H3N2) dilution solution up to $4 \times 10^4$ fold, a color change was observed only in the type A detection zone; whereas in the case of using the B/Shangdong/7/97 dilution solution up to $4 \times 10^3$ fold, a color change was observed only in the type B detection zone.

Liquid sample test kits were prepared from the membrane carriers prepared as in Experimental Examples 1 to 24, as mentioned above. Then, a maximum dilution rate (maximum visible-determination allowable dilution rate of type A) at which the presence or absence of a colored line cannot be visually observed 15 minutes after initiation of the test was obtained by increasing the dilution rate of type A influenza virus A/Beijing/32/92 (H3N2) from $4 \times 10^4$. A test was carried out at a 1/2 dilution rate as low as the maximum dilution rate to obtain the time (time until stabilization of color concentration of type A) until a stable colored line was obtained from initiation of the test. The results are shown in Tables 1 to 3.

Liquid sample test kits were prepared from the membrane carriers prepared as in Experimental Examples 1 to 24, as mentioned above. Then, a maximum dilution rate (maximum visible-determination allowable dilution rate of type B) at which the presence or absence of a colored line cannot be visually observed was obtained when the dilution rate of type B influenza virus B/Shangdong/7/97 was increased from $4 \times 10^-$. A test was carried out at a 1/2 dilution rate as low as the maximum dilution rate to obtain the time (time until stabilization of color concentration of type B) until a stable colored line was obtained from initiation of the test. The results are shown in Tables 1 to 3.

As the time until a stable colored line was obtained, an average value of the time until a stable colored line was obtained in type A and the time until a stable colored line was obtained in type B, was used.

In Tables 1 to 3, the results of overall evaluations on Experimental Examples based on the following criteria are also shown.

A: Determination can be made at a dilution rate of $5 \times 10^4$ or more in type A and a dilution rate of $5 \times 10^3$ or more in type B within 4 minutes, or determination can be made at a dilution rate of $7 \times 10^4$ or more in type A and a dilution rate of $7 \times 10^3$ or more in type B within 6 minutes.

B: Overall evaluation of neither A or C is applied.

C: Determination time was 7 minutes or more or the dilution rate at which determination can be made is $4 \times 10^4$ or less in type A or $4 \times 10^3$ or less in type B.

Experimental Examples 25 to 45

Membrane carriers of Experimental Examples 25 to 45 were prepared in the same manner as in Experimental Example 1 except that the nearest distance between microstructures (convex portions) in regions A to C, the diameters and height of convex portions shown in Table 4 were employed.

Preparation of a detection zone, preparation of a label and detection evaluation were carried out in the same manner as in Experimental Examples 1 to 24 except that the particles to be used were changed from the colored latex particles to fluorescent latex particles (micromer-F fluorescent latex particles, material: polystyrene, manufactured by Corefront Corporation), and that the dilution rate (maximum fluorescence determination allowable dilution rate) at which the presence or absence of a colored line cannot be read by an immunochromato reader (C11787 manufactured by Hamamatsu Photonics K. K.) 4 minutes after initiation of the test was obtained. The results were shown in Tables 4 and 5.

In Tables 4 and 5, overall evaluations on Experimental Examples based on the following criteria are also shown.

A: Maximum fluorescence determination allowable dilution rate 4 minutes after initiation of the test is $3 \times 10^6$ or more in type A and $3 \times 10^5$ or more in type B.

B: Overall evaluation of neither A or C is applied.

C: Maximum fluorescence determination allowable dilution rate 4 minutes after initiation of the test is less than $2 \times 10^6$ in type A or less than $2 \times 10^5$ in type B.

TABLE 4

|  | Experimental Example 25 | Experimental Example 26 | Experimental Example 27 | Experimental Example 28 | Experimental Example 29 |
|---|---|---|---|---|---|
| Nearest distance (μm) between microstructures (convex portions) in region A | 5 | 5 | 5 | 5 | 5 |
| Nearest distance (μm) between microstructures (convex portions) in region B | 5 | 5 | 5 | 5 | 5 |
| Nearest distance (μm) between microstructures (convex portions) in region C | 5 | 5 | 5 | 5 | 5 |
| Diameter (μm) of convex portions in region A | 100 | 250 | 250 | 100 | 500 |
| Height (μm) of convex portions in region A | 100 | 250 | 250 | 100 | 500 |
| Diameter (μm) of convex portions in region B | 30 | 30 | 10 | 10 | 10 |
| Height (μm) of convex portions in region B | 30 | 30 | 10 | 10 | 10 |
| Diameter (μm) of convex portions in region C | 100 | 250 | 250 | 100 | 500 |
| Height (μm) of convex portions in region C | 100 | 250 | 250 | 100 | 500 |
| Aspect ratio | 1 | 1 | 1 | 1 | 1 |
| Average flow rate (mm/s) in region A | 3.2 | 3.5 | 3.5 | 3.2 | 3.7 |

TABLE 4-continued

|  | | | | | |
|---|---|---|---|---|---|
| Average flow rate (mm/s) in region B | 2.5 | 2.5 | 1.2 | 1.2 | 1.2 |
| Average flow rate (mm/s) in region C | 3.2 | 3.5 | 3.5 | 3.2 | 3.7 |
| Flow-rate ratio | 1.3 | 1.4 | 2.9 | 2.7 | 3.1 |
| Maximum visible-determination allowable dilution rate of type A 4 minutes after initiation of test | $3 \times 10^6$ | $3 \times 10^6$ | $2 \times 10^6$ | $2 \times 10^6$ | $2 \times 10^6$ |
| Maximum visible-determination allowable dilution rate of type B 4 minutes after initiation of test | $3 \times 10^5$ | $3 \times 10^5$ | $2 \times 10^5$ | $2 \times 10^5$ | $2 \times 10^5$ |
| Overall evaluation | A | A | B | B | B |
| Note | Example | Example | Example | Example | Example |

|  | Experimental Example 30 | Experimental Example 31 | Experimental Example 32 | Experimental Example 33 | Experimental Example 34 | Experimental Example 35 |
|---|---|---|---|---|---|---|
| Nearest distance (μm) between microstructures (convex portions) in region A | 5 | 5 | 5 | 5 | 5 | 5 |
| Nearest distance (μm) between microstructures (convex portions) in region B | 5 | 5 | 5 | 5 | 5 | 5 |
| Nearest distance (μm) between microstructures (convex portions) in region C | 5 | 5 | 5 | 5 | 5 | 5 |
| Diameter (μm) of convex portions in region A | Serially reduced by 4.7 from 100 | Serially reduced by 14.7 from 250 | 50 | 50 | 500 | 100 |
| Height (μm) of convex portions in region A | Serially reduced by 4.7 from 100 | Serially reduced by 14.7 from 250 | 100 | 100 | 100 | 100 |
| Diameter (μm) of convex portions in region B | 30 | 30 | 15 | 300 | 300 | 200 |
| Height (μm) of convex portions in region B | 30 | 30 | 30 | 30 | 30 | 100 |
| Diameter (μm) of convex portions in region C | Serially reduced by 7 from 100 | Serially reduced by 22 from 250 | 50 | 50 | 500 | 100 |
| Height (μm) of convex portions in region C | Serially reduced by 7 from 100 | Serially reduced by 22 from 250 | 100 | 100 | 100 | 100 |
| Aspect ratio | 1 | 1 | 2 | 0.1-2 | 0.1-0.2 | 0.5-1 |
| Average flow rate (mm/s) in region A | 3.0 | 3.2 | 3.6 | 3.7 | 3.0 | 3.2 |
| Average flow rate (mm/s) in region B | 2.5 | 2.5 | 2.7 | 1.3 | 1.3 | 2.4 |
| Average flow rate (mm/s) in region C | 2.7 | 3.0 | 3.6 | 3.7 | 3.0 | 3.2 |
| Flow-rate ratio | 1.2 | 1.3 | 1.3 | 2.8 | 2.3 | 1.3 |
| Maximum visible-determination allowable dilution rate of type A 4 minutes after initiation of test | $3 \times 10^6$ | $3 \times 10^6$ | $3 \times 10^6$ | $2 \times 10^6$ | $2 \times 10^6$ | $3 \times 10^6$ |
| Maximum visible-determination allowable dilution rate of type B 4 minutes after initiation of test | $3 \times 10^5$ | $3 \times 10^5$ | $3 \times 10^5$ | $2 \times 10^5$ | $2 \times 10^5$ | $3 \times 10^5$ |
| Overall evaluation | A | A | A | B | B | A |
| Note | Example | Example | Example | Example | Example | Example |

TABLE 5

|  | Experimental Example 36 | Experimental Example 37 | Experimental Example 38 | Experimental Example 39 | Experimental Example 40 |
|---|---|---|---|---|---|
| Nearest distance (μm) between microstructures (convex portions) in region A | 5 | 5 | 5 | 5 | 5 |
| Nearest distance (μm) between microstructures | 5 | 5 | 5 | 30 | 100 |

TABLE 5-continued

| | | | | | |
|---|---|---|---|---|---|
| (convex portions) in region B | | | | | |
| Nearest distance (μm) between microstructures (convex portions) in region C | 5 | 5 | 5 | 5 | 5 |
| Diameter (μm) of convex portions in region A | 100 | Serially increased by 10 from 100 | Serially increased by 26.7 from 100 | 100 | 100 |
| Height (μm) of convex portions in region A | 100 | 100 | 100 | 100 | 100 |
| Diameter (μm) of convex portions in region B | 500 | 250 | 500 | 100 | 100 |
| Height (μm) of convex portions in region B | 100 | 100 | 100 | 100 | 100 |
| Diameter (μm) of convex portions in region C | 100 | Serially increased by 15 from 100 | Serially increased by 40 from 100 | 100 | 100 |
| Height (μm) of convex portions in region C | 100 | 100 | 100 | 100 | 100 |
| Aspect ratio | 0.2-1 | 0.4-1 | 0.2-1 | 1 | 1 |
| Average flow rate (mm/s) in region A | 3.2 | 3.0 | 2.9 | 3.2 | 3.2 |
| Average flow rate (mm/s) in region B | 2.0 | 2.8 | 2.4 | 1.0 | 0.33 |
| Average flow rate (mm/s) in region C | 3.2 | 2.9 | 2.7 | 3.2 | 3.2 |
| Flow-rate ratio | 1.6 | 1.1 | 1.2 | 3.2 | 9.7 |
| Maximum visible-determination allowable dilution rate of type A 4 minutes after initiation of test | $3 \times 10^6$ | $3 \times 10^6$ | $2 \times 10^6$ | $2 \times 10^6$ | $3 \times 10^6$ |
| Maximum visible-determination allowable dilution rate of type B 4 minutes after initiation of test | $3 \times 10^5$ | $3 \times 10^5$ | $2 \times 10^5$ | $2 \times 10^5$ | $3 \times 10^5$ |
| Overall evaluation | A | A | B | B | A |
| Note | Example | Example | Example | Example | Example |

| | Experimental Example 41 | Experimental Example 42 | Experimental Example 43 | Experimental Example 44 | Experimental Example 45 |
|---|---|---|---|---|---|
| Nearest distance (μm) between microstructures (convex portions) in region A | 5 | 5 | 5 | 5 | Serially increased by 1.7 from 5 |
| Nearest distance (μm) between microstructures (convex portions) in region B | 100 | 500 | 100 | 250 | 30 |
| Nearest distance (μm) between microstructures (convex portions) in region C | 5 | 5 | 5 | 5 | Serially increased by 2.5 from 5 |
| Diameter (μm) of convex portions in region A | 500 | 500 | 250 | 250 | 100 |
| Height (μm) of convex portions in region A | 500 | 500 | 250 | 250 | 100 |
| Diameter (μm) of convex portions in region B | 500 | 500 | 250 | 250 | 100 |
| Height (μm) of convex portions in region B | 500 | 500 | 250 | 250 | 100 |
| Diameter (μm) of convex portions in region C | 500 | 500 | 250 | 250 | 100 |
| Height (μm) of convex portions in region C | 500 | 500 | 250 | 250 | 100 |
| Aspect ratio | 1 | 1 | 1 | 1 | 1 |
| Average flow rate (mm/s) in region A | 3.7 | 3.7 | 3.5 | 3.5 | 2.5 |
| Average flow rate (mm/s) in region B | 1.5 | 0.37 | 0.40 | 0.35 | 1.0 |
| Average flow rate (mm/s) in region C | 3.7 | 3.7 | 3.5 | 3.5 | 2.1 |
| Flow-rate ratio | 2.5 | 10.0 | 8.8 | 10.0 | 2.5 |
| Maximum visible-determination allowable dilution rate of type A 4 minutes after initiation of test | $2 \times 10^6$ | $3 \times 10^6$ | $3 \times 10^6$ | $3 \times 10^6$ | $2 \times 10^6$ |

TABLE 5-continued

| | | | | | |
|---|---|---|---|---|---|
| Maximum visible-determination allowable dilution rate of type B 4 minutes after initiation of test | $2 \times 10^5$ | $3 \times 10^5$ | $3 \times 10^5$ | $3 \times 10^5$ | $2 \times 10^5$ |
| Overall evaluation | B | A | A | A | B |
| Note | Example | Example | Example | Example | Example |

The results of Tables 1 to 3 show that, in the liquid sample test kit of the embodiment, the flow rate can be controlled by varying the height, bottom area, nearest distance and aspect ratio of the microstructures in the flow path. As a result, it was shown that, in the embodiment, the time until stabilization of sensitivity of the liquid sample test kit and color can be controlled, and that a highly sensible test can be carried out in a short time. From the results of Tables 4 and 5, it was confirmed that, in the liquid sample test kit, even if fluorescent latex particles are used, a highly sensitivity test can be carried out.

INDUSTRIAL APPLICABILITY

The liquid sample test kit according to the embodiment enables implementation of a highly sensible test in a short time at low cost and is thus useful as a disposable POCT reagent.

REFERENCE SIGNS LIST

2: Flow path, 3,3a, 13: Membrane carrier having microstructures provided therein, 3x,13x: Drop zone, 3y,13y: Detection zone, 4,4a,4b,4c,4d: Representative length of the bottom surface of a convex portion (diameter of convex-portion bottom), 4A: Representative length of the bottom surface of a front portion (upstream of the transport direction) of a site where microstructures change (diameter of convex-portion bottom in first region A), 4B: Representative length of the bottom surface of a rear portion of a site where microstructures change (diameter of convex-portion bottom in second region B), 4C: Representative length of the bottom surface of a rear portion of a site where microstructures change (diameter of convex-portion bottom in third region C), 5: Nearest distance between microstructures, 5A: Nearest distance between microstructures in the front portion of a site where microstructures change (nearest distance between microstructures (convex portions)) in first region A), 5B: Nearest distance between microstructures in the rear portion of a site where microstructures change (nearest distance between microstructures (convex portions) in second region B), 5C: Nearest distance between microstructures in the rear portion of a site where microstructures change (nearest distance between microstructures (convex portions) in third region C), 5D: Buffer distance (buffer distance at a site where microstructures change), 6,6a,6b, 6c,6d: Height of convex portions, 7,7a,7b,7c,7d: Microstructure, 8,8a,8b,8c,8d: Convex portion, 9: Flat part, 10,10a, 10b, 10c, 10d: Bottom surface of convex portions, 18: Test kit for liquid sample, 18a: Case, 18b: First opening, 18c: Second opening, 20: Mold, 20A: A predetermined side, 20B: Opposite side to the predetermined side, A: First region, B: Second region, C: Third region, d: Liquid sample flow direction (transport direction).

The invention claimed is:

1. A membrane carrier for a liquid sample test kit for detecting a target substance in a liquid sample, comprising at least one flow path transporting the liquid sample, wherein:
    a microstructure producing capillary action for transporting the liquid sample is formed at a bottom of the flow path,
    the membrane carrier has a first region A, a second region B and a third region C, wherein the first region A and second region B are adjacent to each other, the second region B and third region C are adjacent to each other, and the microstructure is mutually different between adjacent regions,
    the microstructure has a plurality of convex portions, wherein the shape of the plurality of convex portions is a cone, a polygonal pyramid, a truncated cone, a truncated polygonal pyramid, a cylinder, a hemisphere or a semi-ellipsoid, and
    a detection substance detecting a target substance is immobilized in the second region B.

2. The membrane carrier for a liquid sample test kit according to claim 1, wherein the microstructure is provided such that a flow rate of the liquid sample in the flow path changes within the flow path.

3. The membrane carrier for a liquid sample test kit according to claim 1, wherein the microstructure is provided such that a ratio of a highest flow rate to a lowest flow rate of the liquid sample in the flow path is 1 or more and 10 or less.

4. The membrane carrier for a liquid sample test kit according to claim 1, wherein the microstructure is provided such that both of a lowest flow rate and a highest flow rate of the liquid sample in the flow path are 0.30 mm/s or more and 5.0 mm/s or less.

5. The membrane carrier for a liquid sample test kit according to claim 1, wherein a height of the microstructure in the flow path is 10 μm or more and 500 μm or less.

6. The membrane carrier for a liquid sample test kit according to claim 1, wherein a bottom area of the microstructure in the flow path is 75 μm² or more and 250000 μm² or less.

7. The membrane carrier for a liquid sample test kit according to claim 1, wherein a nearest distance between the convex portions in the flow path is 500 μm or less.

8. The membrane carrier for a liquid sample test kit according to claim 1, wherein an aspect ratio of the microstructure is 0.1 or more and 2.0 or less.

9. A liquid sample test kit for detecting a target substance in a liquid sample, comprising the membrane carrier for a liquid sample test kit according to claim 1, wherein
    the membrane carrier comprises a detection zone in the second region B for detecting the target substance in the liquid sample, and
    a color change occurs when the target substance is detected in the detection zone.

10. The liquid sample test kit according to claim 9, wherein a label comprising an antibody or an antigen-binding fragment thereof specifically reacting with the target substance in the liquid sample is provided in at least a part of the liquid sample test kit to be able to react with the target substance, and the color change is produced by the label bound to the target substance.

11. The liquid sample test kit according to claim 10, wherein the label is a particle comprising a colored latex particle or a fluorescent latex particle to which the antibody or the antigen-binding fragment thereof binds.

12. The liquid sample test kit according to claim 10, wherein the detection substance detecting the target substance is immobilized in the detection zone, and the color change is produced by holding the label by the detection substance in the detection zone to produce a color.

13. A method for producing the liquid sample test kit according to claim 9, comprising immobilizing, to the detection zone, a detection substance producing the color change by holding the target substance in the detection zone.

14. A method for testing a liquid sample using the liquid sample test kit according to claim 9, the method comprising:

preparing a mixed liquid sample by mixing the liquid sample and a label specifically binding to a target substance in the liquid sample to mutually bind the target substance and the label;

delivering a drop of the mixed liquid sample to a drop zone provided in the membrane carrier;

transporting the mixed liquid sample from the drop zone to the detection zone by the microstructure; and detecting a color change in the detection zone.

* * * * *